United States Patent [19]

Harbeson et al.

[11] Patent Number: 5,541,290
[45] Date of Patent: Jul. 30, 1996

[54] OPTICALLY PURE CALPAIN INHIBITOR COMPOUNDS

[76] Inventors: Scott L. Harbeson, 203 Pemberton St., Apt. 5, Cambridge, Mass. 02140; Julie A. Straub, 16 Plato Ter., Winchester, Mass. 01890

[21] Appl. No.: 82,274

[22] Filed: Jun. 24, 1993

[51] Int. Cl.⁶ .............................. A61K 38/04; C07K 5/00
[52] U.S. Cl. ..................... 530/330; 530/331; 544/106
[58] Field of Search ................................. 530/330, 331; 514/18, 19; 544/106

[56] References Cited

U.S. PATENT DOCUMENTS

| | | | |
|---|---|---|---|
| 5,371,072 | 12/1994 | Webb et al. | 514/18 |
| 5,444,042 | 8/1995 | Bartus et al. | 514/2 |

FOREIGN PATENT DOCUMENTS

| | | |
|---|---|---|
| 0195212A2 | 2/1986 | European Pat. Off. . |
| 0364344A2 | 6/1989 | European Pat. Off. . |
| 0363284A2 | 6/1989 | European Pat. Off. . |
| 468339A2 | 1/1992 | European Pat. Off. . |
| 04001140 | 1/1992 | Japan . |
| 04149166 | 5/1992 | Japan . |
| 90/12805 | 1/1990 | WIPO . |
| PCT/US91/ 09786 | 12/1991 | WIPO . |
| PCT/US91/ 09801 | 12/1991 | WIPO . |
| 92/11850 | 7/1992 | WIPO . |
| 94/00095 | 1/1994 | WIPO . |

OTHER PUBLICATIONS

U.S. Ser. No. 07/682,925 Apr. 9, 1991 Bartus et al.
U.S. Ser. No. 07/635,952 Dec. 28, 1990 Bartus et al.
U.S. Ser. No. 07/816,120 Dec. 27, 1991 Bartus et al.
U.S. Ser. No. 07/635,287 Dec. 12, 1990 Powers.
M. Robert Leanna et al., Synthesis of α–Amino and α–Alkoxy Aldehydes via Oxoammonium Oxidation, *Tetrahedron Letters*, 33, (35):5029 . 5032 (1992).

Lain–Yen Hu and Robert H. Abeles, Inhibition of Cathepsin B and Papain and Peptidyl α–Keto Esters, α–Keto Amides, α–Diketones, and α–Keto Acids, *Archives of Biochemistry and Biophysics*, 281, (2):271–274 (Sep. 1990).

α–Diketone and α–Keto Ester Derivatives of N–Protected Amino Acids and Peptides as Novel Inhibitors of Cysteine and Serine Proteinases, Communications to the Editor, *J. Med. Chem.*, 33:11–13 (1990).

T. D. Ocain et al., α–Keto Amide Inhibitors of Aminopeptidase, *J. Med. Chem.*, 35:451–456 (1992).

*Primary Examiner*—Christine M. Nucker
*Assistant Examiner*—Benet Prickril
*Attorney, Agent, or Firm*—Townsend and Townsend and Crew LLP

[57] ABSTRACT

Optically pure α-ketoamide compounds, and use therefor in treating neurodegenerative pathologies having enhanced Calpain activity, are disclosed. These compounds comprise optically pure α-ketoamides, and physiologically acceptable salts thereof, wherein the α-ketoamide contains an amino acid isomer which has an L-configuration about the chiral center which is structurally located in the α position to the ketone of the α-ketoamide, and wherein the amide functionality of the α-ketoamide portion of the compound's molecule is derived from an amine of an amino acid or an amine substituted with a sulfone functionality. The method of treating a human neurodegenerative pathology, having enhanced Calpain activity, with a Calpain inhibitor composition while reducing undesirable inhibition of other cysteine proteases and other side effects associated with the racemic calpain inhibitor composition includes administering an optically pure L-isomer of an α-ketoamide compound, wherein the L-isomer is substantially free of its D-isomer. The method of forming an optically pure L-α-ketoamide includes mixing an L-β-amino-α-hydroxyamide in a solution containing a free radical catalyst and then mixing an oxidizing agent into said solution under conditions sufficient to form said optically pure L-α-ketoamide.

13 Claims, No Drawings

OPTICALLY PURE CALPAIN INHIBITOR COMPOUNDS

BACKGROUND OF THE INVENTION

The present invention relates generally to the field of neuroprotectants and more specifically to the use of inhibitors of calcium-stimulated proteases, such as calpain, as therapeutics for neurodegeneration.

Neural tissues, including brain, are known to possess a large variety of proteases, including at least two calcium-stimulated proteases, termed Calpain I and Calpain II, which are activated by micromolar and millimolar $Ca^{+2}$ concentrations, respectively. Calpains are a family of calcium activated thiol proteases that are present in many tissues. Calpain II is the predominant form, but Calpain I is found at synapses and is thought to be the form involved in long term potentiation and synaptic plasticity.

Thiol proteases are distinguished from serine proteases, metalloproteases and other proteases by their mechanism of action and by the amino acid residue (cysteine) that participates in substrate attack. Although several thiol proteases are produced by plants, these proteases are not common in mammals, with cathepsin B (a lysosomal enzyme), other cathepsins and the calpains being among the few representatives of this family that have been described in mammals. Calpain I and Calpain II are the best described of these, but several other members of the cysteine protease family have been reported.

Other $Ca^{2+}$ activated thiol proteases may exist, such as those reported by Yoshihara et al. in J. Biol. Chem. 265:5809–5815 (1990). The term "Calpain" is used hereinafter to refer to any $Ca^{+2}$ activated thiol proteases including the Yoshihara enzyme and Calpains I and II.

While Calpains degrade a wide variety of protein substrates, cytoskeletal proteins seem to be particularly susceptible to attack. In at least some cases, the products of the proteolytic digestion of these proteins by Calpain are distinctive and persistent over time. Since cytoskeletal proteins are major components of certain types of cells, this provides a simple method of detecting Calpain activity in cells and tissues. Specifically, the accumulation of the breakdown products ("BDP's") of spectrin, a cytoskeletal protein, has been associated with the activation of Calpain. In neural tissues, activation of Calpains, as evidenced by accumulation of these BDP's has been observed in many neurodegenerative conditions, including denervation resulting from focal electrolytic lesions, genetic abnormalities, excitotoxicity, Alzheimer's disease, following ischemia in gerbils and following administration of the toxins kainate and colchicine in rats, when administered peripherally or centrally.

Currently available Calpain inhibitors, which can cross the blood-brain barrier to inhibit Calpain in Central Nervous System (CNS) tissue, typically have limited solubility, thus making parenteral administration very difficult. Also may of these inhibitors are not calpain-specific and will inhibit a wide variety or proteases in addition to calpain.

Thus a need exists for calpain inhibitor compounds that possess good membrane permeability, are calpain-specific and have good solubility to permit parenteral administration.

SUMMARY OF THE INVENTION

This invention pertains to optically pure α-ketoamide compounds and use therefor in treating neurodegenerative pathologies having enhanced Calpain activity. The compounds of the present invention comprise optically pure α-ketoamides, and physiologically acceptable salts thereof, wherein the α-ketoamide contains an amino acid which has an L-configuration about the chiral center which is structurally located in the α position to the ketone of the α-ketoamide, and wherein the amide functionality of the α-ketoamide portion of the compound's molecule is derived from an amine of an amino acid or an amine substituted with a sulfone functionality.

The invention also includes a method of treating a human and mammalian neurodegenerative pathologies, having enhanced Calpain activity, with a Calpain inhibitor composition, while reducing undesirable inhibition of other catalytic proteases and other side effects associated with the racemic Calpain inhibitor composition. This method comprises administering an optically pure L-isomer of an α-ketoamide compound, wherein the L-isomer is substantially free of its D-isomer.

The invention also pertains to a method of forming an optically pure D- or L-α-ketoamide by mixing an β-amino-α-hydroxyamide in a solution containing a free radical catalyst and then mixing an oxidizing agent into said solution under conditions sufficient to form said optically pure α-ketoamide.

The compounds of this invention have the advantage that these compounds have increased selectivity for Calpain over other protease enzymes and have greater solubility, thus enhancing the ability to provide effective parenteral administration. The method of treatment with optically pure L-α-ketoamides has the advantage of effectively treating human neurodegenerative pathologies, such as stroke, head trauma, Alzheimer's and neural damage due to ischemia, while reducing the side-effects associated with the racemate.

DETAILED DESCRIPTION OF THE INVENTION

The features and other details of the invention, either as steps of the invention or as combinations of parts of the invention, will now be more particularly described and pointed out in the claims. It is understood that the particular embodiments of the invention are shown by way of illustration and not as limitations of the invention. The principle features of this invention can be employed in various embodiments without departing from the scope of the invention.

The present invention relates to the composition and/or methods of forming and using optically pure α-ketoamide compounds, represented by the following structural formulae I, II, III, IV, V and VI:

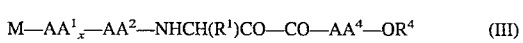

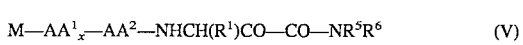

For each formula shown above, M represents H, $NH_2$—CO—, $NH_2$—CS—, $NH_2$-$SO_2$—, $R^7$—NH—CO—, $R^7_2$N—CO—, $R^7$—NH—CS—, $R^7_2$N—CS—, $R^7$—NH—$SO_2$—, $R^7_2$N—$SO_2$—, $R^7$—CO—, $R^7$—CS—, $R^7$—$SO_2$—, $C_6H_5CH_2$—O—CO  $R^7$—O—CO—, $R^7$—O—CS—, $R^8N$—CO—, $R^8N$—CS— or $R^8N$—SO$_2$—.

$R^7$ is a $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluoroalkyl, phenyl substituted n times with K, naphthyl substituted n times with K, $C_{1-10}$ alkyl with an attached phenyl group substituted n times with K, $C_{1-10}$ alkyl with two attached phenyl groups substituted n times with K, $C_{1-10}$ alkyl with an attached phenoxy group, or $C_{1-10}$ alkyl with an attached phenoxy group substituted n times with K on the phenoxy group, while n is 0, 1, 2 or 3.

J is a halogen, hydroxyl, carboxy, cyano, amino, nitro, $C_{1-10}$ alkyloxy, $C_{1-10}$ alkylamino, $C_{2-12}$ dialkylamino, $C_{1-10}$ alkoxy—CO— group, $C_{1-10}$ alkoxy—NH— group, $C_{1-10}$ alkyl-S-group, or $C_{1-10}$ alkyl-SO$_2$— group.

K is a halogen, hydroxyl, carboxy, cyano, amino, nitro, $C_{1-10}$ alkyl, $C_{1-10}$ perfluoroalkyl, $C_{1-10}$ alkylamino, $C_{2-12}$ dialkylamine, $C_{1-10}$ alkoxy-CO— group, $C_{1-10}$ acyl, $C_{1-10}$ alkyloxy group, $C_{1-10}$ alkyl-S— group or $C_{1-10}$ alkyl-SO$_2$— group.

$R^8N$ is a $C_{3-6}$ saturated or unsaturated heterocycle containing at least one nitrogen atom. Said heterocycle can contain Q additional heteroatoms selected from the group consisting of nitrogen, oxygen, sulfur and combinations thereof. Further, said heterocycle can be substituted with one or more substituents selected from the group consisting of a hydroxyl, halogen, alkyl, cycloalkyl, aryl, alkoxy, alkoxycarbonyl, alkylthio and amino. Q is 0, 1 or 2.

$AA^1$ is an amino acid residue of a side chain blocked or unblocked amino acid, with the L configuration, D configuration or no chirality at the α-carbon, wherein said amino acid is selected from the group consisting of alanins, valine, leucine, isoleucine, proline, methionine, methionine sulfone, methionine sulfoxide, phenylalanine, tryptophan, glycine, serine, threonine, cysteine, tyrosine, asparagine, glutamine, aspartic acid, glutamic acid, lysine, arginine, histidine, phenylglycine, β-alanins, norleucine, norvaline, α-aminobutyric acid, ε-aminocaproic acid, citrulline, hydroxyproline, ornithine, homoarginine, sarcosine, indoline-2-carboxylic acid, 2-azetidine-carboxylic acid, pipecolinic acid, O-methylserine, O-ethylserine, S-methylcysteine, S-ethylcysteine, S-benzylcysteine, S-methylcysteine sulfone, S-ethylcysteine sulfone, S-benzyl-cysteine sulfone, cyclohexylalanine, homophenylalanine, p-chloro-phenylalanine, p-nitro-phenylalanine, p-amino-phenylalanine, 4-methoxy-phenylalanine, thienylalanine, pyridylalanine, NH$_2$—CH(CH$_2$CH(CH$_2$CH$_3$)$_2$)—COOH, α-aminoheptanoic acid, NH$_2$—CH(CH$_2$-1-naphthyl)—COOH, NH$_2$—CH(CH$_2$-2-naphthyl)—COOH, NH$_2$—CH(CH$_2$-cyclohexyl)—COOH, NH$_2$—CH(CH$_2$-cyclopentyl)—COOH, NH$_2$—CH(CH$_2$-cyclobutyl)—COOH, NH$_2$—CH(CH$_2$-cyclopropyl-butyl)—COOH, trifluoroleucine or hexafluoroleucine.

An amino acid residue is defined herein by the structural formula

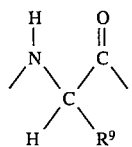

and isomers thereof, wherein $R^9$ is the side chain of the amino acid residue. For example, $R^9$ for leucine is (CH$_3$)$_2$CHCH$_2$, $R^9$ for cysteine is HSCH$_2$, $R^9$ for alanine is CH$_3$ and $R^9$ for phenylalanine is C$_6$H$_5$CH$_2$.

X is 0, 1, 2 or 3.

NHCH($R^1$)CO is a side chain blocked or unblocked amino acid with the L configuration and wherein $R^1$ is a branched or unbranched $C_{1-8}$ alkyl, cycloalkyl of fluoroalkyl.

$R^2$ is a branched or unbranched, saturated or unsaturated constituent selected from the group consisting of $C_{1-20}$ alkyl, $C_{3-20}$ cycloalkyl, $C_{1-20}$ alkyl with an attached phenyl group which is substituted n times with K, and $C_{1-20}$ cycloalkyl with an attached phenyl group which is substituted n times with K, and wherein said constituent can be substituted one or more times with Z.

Z is a hydroxyl, carboxy, alkoxy, alkoxymethoxy, alkanoate, alkyl, carbamyl, —O—CH$_2$—SO$_2$—CH$_3$ group, —OCH$_2$CH$_2$—O—CH$_2$CH$_2$—OH group, or —OCH$_2$CH$_2$—O—CH$_2$CH$_2$—OCH$_3$ group.

$R^3$ is $R^2$, —OH, —OR$^2$, NH$_2$, NHR$^2$ or NR$^2$R$^2$.

$AA^2$ is an amino acid residue of a side chain blocked or unblocked amino acid, with the L or D configuration at the a-carbon, wherein said amino acid residue imparts calpain-specificity to calpain inhibitor molecules. Examples of amino acid residues, which are suitable to impart calpain selectivity, include leucine, isoleucine or valine.

$AA^3$ is an amino acid residue of a side chain blocked or unblocked amino acid, with the L configuration at the α-carbon, wherein said amino acid is selected from the group consisting of alanine, α-aminobutyric acid, norvaline, valine, norleucine, leucine, phenylalanine, tyrosine, cyclohexylalanine, homophenylalanine, p-chloro-phenylalanine, p-nitro-phenylalanine, p-amino-phenylalanine, thienylalanine, lysine, ornithine, aspartic acid, glutamic acid, serine, threonine, pyridylalanine or 4-methoxy-phenylalanine or NACH($R^1$)CO.

$AA^4$ is an amino acid residue of a side chain blocked or unblocked amino acid, with the L configuration, D configuration or no chirality at the α-carbon, wherein said amino acid is selected from the group consisting of glycine, β-alanine, alanine, α-aminobutyric acid, norvaline, valine, norleucine, leucine, phenylalanine, tyrosine, cyclohexylalanine, homophenylalanine, p-chloro-phenylalanine, p-nitro-phenylalanine, p-amino-phenylalanine, thienylalanine, lysine, ornithine, aspartic acid, glutamic acid, serine, threonine, pyridylalanine or 4-methoxy-phenylalanine.

$R^4$ is H, $C_{1-20}$ alkyl, aryl, $C_{1-20}$ alkyl with an attached phenyl group, or $C_{1-20}$ alkyl with an attached phenyl group substituted with K.

$R^5$ and $R^6$ are selected independently from the group consisting of H, $C_{1-20}$ alkyl, $C_{3-20}$ cycloalkyl, $C_{1-20}$ alkyl with an attached phenyl group which is substituted n times with K, and $C_{3-20}$ cycloalkyl with an attached phenyl group which is substituted n times with K, $C_{1-10}$ alkyl substituted with the nitrogen atom of a morpholine ring, $C_{1-10}$ alkyl substituted with the nitrogen atom of a piperidine ring, $C_{1-10}$ alkyl substituted with the nitrogen atom of a pyrrolidine ring, $C_{1-20}$ alkyl substituted with a hydroxyl group, $C_{1-10}$ alkyl substituted with a 2-pyridyl group, $C_{1-10}$ alkyl substituted with a 3-pyridyl group, $C_{1-10}$ alkyl substituted with a 4-pyridyl group, $C_{1-10}$ alkyl substituted with a cyclohexyl group, —NH—CH$_2$CH$_2$-(4-hydroxyphenyl) and —NH—CH$_2$CH$_2$-(3-indolyl).

As defined herein, an optically pure α-ketoamide compound is an α-ketoamide containing an amino acid that has an L-configuration about the chiral center which is structurally located in the a position to the ketone of the α-ketoamide.

In the method for forming optically pure isomers of α-ketoamides with structural formulae I–VI, a β-amino-α-hydroxyamide, which is optically pure at the β carbon (D or L configuration), is exposed to oxidizing conditions sufficient to form the associated optically pure α-ketoamide.

Suitable α-hydroxyamides are represented by the formulae VII, VIII, IX, X, XI and XII, shown below:

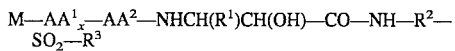
$$M—AA^1_x—AA^2—NHCH(R^1)CH(OH)—CO—NH—R^2—SO_2—R^3 \quad (VII)$$

$$M—AA^1_x—AA^2—AAH—CO—NH—R^2—SO_2—R^3 \quad (VIII)$$

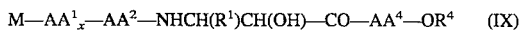
$$M—AA^1_x—AA^2—NHCH(R^1)CH(OH)—CO—AA^4—OR^4 \quad (IX)$$

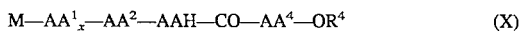
$$M—AA^1_x—AA^2—AAH—CO—AA^4—OR^4 \quad (X)$$

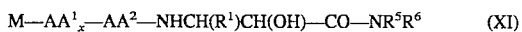
$$M—AA^1_x—AA^2—NHCH(R^1)CH(OH)—CO—NR^5R^6 \quad (XI)$$

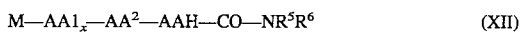
$$M—AA1_x—AA^2—AAH—CO—NR^5R^6 \quad (XII)$$

wherein NHCH(R¹)CH(OH) is an alcohol, with the L configuration at the β carbon, reduced from a side chain blocked or unblocked amino acid residue, wherein R¹ is a branched or unbranched $C_{1-8}$ alkyl, cycloalkyl or fluoroalkyl. The structural formula of NHCH(R¹)CH(OH) is defined herein as

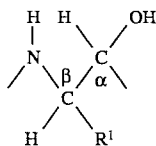

and isomers thereof.

AAH is an alcohol, with the L configuration at the β-carbon, reduced from a side chain blocked or unblocked amino acid residue of an amino acid, wherein said amino acid is selected from the group consisting of alanine, α-aminobutyric acid, norvaline, valine, norleucine, leucine, phenylalanine, tyrosine, cyclohexylalanine, homophenylalanine, p-chloro-phenylalanine, p-nitro-phenylalanine, p-amino-phenylalanine, thionylalanine, lysine, ornithine, aspartic acid, glutamic acid, serine, threonine, pyridylalanine or 4-methoxy-phenylalanine. The structural formula of AAH is defined herein as

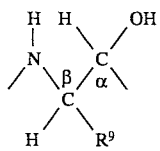

and isomers thereof.

Oxidizing conditions sufficient to form an α-ketoamide include exposing a solvated α-hydroxyamide to an oxidizing agent while in the presence of a free radical catalyst. Suitable solvents for α-hydroxyamides include polar aprotic organic liquids, such as methylene chloride, toluene, diethyl ether, ethyl acetate, acetonitrile, tetrahydrofuran and dioxane. Examples of suitable oxidizing agents include sodium hypochlorite solution and t-butyl-hypochlorite, while suitable free radical catalysts include, for example, 2,2,6,6-tetramethyl-1-piperidinyloxy ("TEMPO") and 4-acetylamino-2,2,6,6-tetramethyl-1-piperidinyloxy.

In one embodiment, a β-amino-α-hydroxyamide, which is optically pure at the β carbon (D or L configuration), TEMPO, potassium bromide (KBr), methylene chloride and water are mixed in a reaction vessel to form a reaction mixture. In a preferred embodiment the reaction mixture contains, for each mmole of β-amino-α-hydroxyamide, about 1–100 mg TEMPO and about 1–50 mg KBr, between about 1–100 ml methylene chloride and between about 1–100 ml of water. It is understood that the components of the reaction mixture can be introduced into the reaction vessel in any order or that some or all components can be mixed together prior to being introduced into the reaction vessel.

The reaction mixture is cooled to a temperature between about –5° to 10° C. and then an oxidizing agent is introduced into to the cooled reaction mixture, while the reaction mixture is vigorously stirred, to form an optically pure α-ketoamide isomer. In one embodiment, between about 1 and 20 mL of a suitable sodium hypochlorite (NaOCl) solution, with a pH between about 4 and about 10, is introduced into the reaction mixture for each mmole of β-amino-α-hydroxyamide contained therein. An example of a suitable NaOCl solution is a solution which is about 5.25% NaOCl. In a preferred embodiment, the NaOCl solution is buffered to a pH of about 9.4 to 9.6. Examples of suitable buffers include, for example, sodium bicarbonate.

It is understood that the oxidizing agent can be introduced into the reaction mixture in aliquots, continuously or in a bulk amount. It is also understood that the reaction mixture can instead be introduced into the oxidizing agent or that the reaction mixture and oxidizing agent can be conjointly introduced into a separate, second reaction vessel.

The reaction mixture can be periodically analyzed for the β-amino-α-hydroxyamide isomer. If the β-amino-α-hydroxyamide isomer is still detected in the reaction mixture, additional free-radical catalyst and/or oxidizing agent can be introduced into the reaction mixture to improve the yield of optically pure α-ketoamide. The further introduction of oxidizing agent and free-radical catalyst to the reaction mixture can be done conjointly, concurrently or sequentially.

In an alternate embodiment, the reaction mixture solidifies following the addition of oxidizing agent. Following solidification, a polar organic solvent is mixed with the reaction mixture to form a slurry. In yet another embodiment, a suitable volume of methylene chloride is mixed with the solid reaction mixture to obtain a slurry. The optically pure α-ketoamide is then separated from the reaction mixture and purified by means known in the art.

The reaction precursor, β-amino-α-hydroxyamide, is derived from a amino acid with a suitable removable protecting group (RPG), such as Boc or Cbz. AN RPG-amino acid is defined herein as an amino acid whose amino group (—NH₂) is substituted with a removable protecting group. A Boc-protected amino acid is defined herein as an amino acid whose amino group (—NH₂) is substituted with a t-butyloxycarboxy group (CH₃C(CH₃)(CH₃)OC(O)—, or "Boc"). A Cbz-protected amino acid is defined herein as an amino acid whose amino group (—NH₂) is substituted with a benzyloxy-carbonyl group (Cbz).

In yet another embodiment, suitable amino acid isomers are amino acid isomers which have an L-configuration about the chiral center which is structurally located in the α position to the amino acid's carboxy group. In a preferred embodiment, suitable Boc-protected amino acid isomers include, for example, Boc-L-leucine, Boc-L-isoleucine, Boc-L-valine, Boc-L-α-aminobutyric acid and Boc-L-phenylalanine.

N,O-dimethylhydroxylamine·HCl (DMHA·HCl) is dissolved in a suitable solvent and then contacted with the RPG-protected amino acid to form the N,O-dimethylhydroxamate. In one embodiment, about 1 to 5 mmole of DMHA·HCl is used per mmole of RPG-amino acid. In another embodiment, the RPG-amino acid is dissolved in about 1 to 5 L of anhydrous tetrahydrofuran (THF) per mole of RPG-amino acid, and then contacted with about 1 to 5 moles of 1,1'-carbonyldiimidazole per mole of RPG-amino acid or with a mixture of about 1 to 5 moles of diisopropylethylamine and about 1 to 5 moles of benzotriazole-1-yloxy-tris-pyrrolidino-phosphonium hexafluorophosphate (PyBOP), prior to being contacted with the DMHA·HCl. In yet another embodiment, the RPG-amino acid is blanketed with an inert gas after dissolution. Suitable anhydrous gases include, for example, argon, nitrogen and dry air.

Suitable solvents for DMHA·HCl include, for example, a mixture of about 0.5 to 1 L dimethylformamide (DMF) per mole DMHA·HCl or about 0.5 to 1 L of 20:1 THF:acetonitrile mix per mole DMHA·HCl. In one embodiment, a volume of diisopropylethylamine (DIEA) sufficient to neutralize the DMHA·HCl salt, typically about one equivalent, is also mixed with the DMHA·HCl before contacting the DMHA·HCl and the RPG-amino acid.

The N,O-dimethylhydroxamate is separated and purified, by known means, and then contacted with a reducing agent under conditions sufficient to form a metal-aldehyde complex. In one embodiment, the N,O-dimethylhydroxamate is dissolved in anhydrous ethyl ether and then contacted about 1 to 2 mole of lithium aluminum hydride (LAH) per mole of N,O-dimethylhydroxamate, which is suspended in anhydrous ethyl ether, to form an aluminum-aldehyde complex. Conditions sufficient to form an aluminum-aldehyde complex include mixing the reducing agent and the dissolved RPG-amino acid at a rate such that the temperature of the reaction mixture does not exceed about 5° C. In another embodiment, conditions sufficient further include blanketing the reaction mixture with an inert gas, such as argon. Subsequently, a neutralizing agent is directed into the reaction mixture to neutralize reducing agent, remaining in the reaction mixture. In one embodiment, ethyl acetate is used to neutralize LAH remaining in the reaction mixture.

The metal-aldehyde complex is then dissociated to form an aldehyde. In one embodiment, a suitable acid, such as hydrochloric acid, is mixed with the aluminum-aldehyde complex under conditions sufficient to dissociate the aluminum-aldehyde complex to form an aldehyde. Conditions sufficient to dissociate include mixing the acid and the reaction mixture at a rate such that the temperature of the reaction mixture does not exceed about 5° C. The aldehyde is then separated and purified, by known means, and subsequently transformed to a cyanohydrin.

In one embodiment, the aldehyde is dissolved in methanol and cooled to about 5° C. About 1 to 5 moles of sodium bisulfite per mole of aldehyde, which is in aqueous solution and is cooled to about 5° C., is then mixed with the aldehyde solution to from a bisulfite adduct. After stirring the bisulfite adduct solution for a suitable period, for example, about 3 to 24 hours, while maintaining temperature at about 5° C., the mixture is combined with about 1 to 5 moles of sodium cyanide, in aqueous solution, per mole of aldehyde to form a cyanohydrin.

The cyanohydrin is mixed with 1,4-dioxane, concentrated HCl and anisole and then is gently refluxed, with stirring, for a suitable period, for example, about 3 to 12 hours to hydrolyze the cyanohydrin to form an α- hydroxy-β-amino acid.

The α-hydroxy-β-amino acid is subsequently isolated, by known means, and then purified by ion exchange column chromatography, using ammonium hydroxide to elute the α-hydroxy-β-amino acid. The α-hydroxy-β-amino acid can then be further modified by coupling reactions.

In one embodiment, an alkyloxycarbonyl-α-hydroxy-β-amino acid is formed from the α-hydroxy-β-amino acid. The α-hydroxy-β-amino acid is dissolved in about 1N NaOH and then mixed with about 1 to 2 moles of di-tert-butyl dicarbonate, dissolved in dioxane, per mole of α-hydroxy-β-amino acid. The reaction mixture is stirred at room temperature for an appropriate period, such as about 4 or more hours, and the pH of the reaction mixture is maintained between about 9.5 to 11 by adding a suitable base, such as 1N NaOH. The reaction mixture is then diluted with deionized water and washed with ethyl ether. The aqueous phase is cooled to about 0° to 10° C. and acidified to a pH of about 2 by adding a suitable acid, such as 1N HCl. The alkyloxycarbonyl-α-hydroxy-β-amino acid is then extracted from the aqueous phase and concentrated by known means.

Each mole of alkyloxycarbonyl-α-hydroxy-β-amino acid is then combined with about one mole of 1-hydroxybenzotriazole (HOBT) in DMF, about 1 to 2 moles of 1-(3-dimethylaminopropyl)-3-ethyl carbodiimide hydrochloride (EDC), and about 1 to 2 moles of ethylamine solution to form a reaction mixture. The reaction mixture is stirred for a suitable period, for example, about 6 or more hours to form an alkyloxycarbonyl-hydroxy ethyl amide. The alkyloxycarbonyl-hydroxy ethyl amide is then separated and purified, by known means, and subsequently reacted with about 4N HCL, which is in 1,4-dioxane, to form an α-hydroxy-β-amino acid ethylamide hydrochloride salt.

The amino group from the β carbon of the α-hydroxy-β-amino acid ethylamide hydrochloride salt is then substituted with a suitable N-substituted leucine group. Suitable N-substituted leucine groups include morpholine-urea-leucine, dimethyl-urea-leucine, Boc-leucine, Cbz-leucine and Boc-leucine. The N-substituted leucine is in a solution containing, about one mole of HOBt per mole of alkyl-leucine, and a 1-methyl-2-pyrrolidinone solvent. For each mole of α-hydroxy-β-amino acid ethylamide hydrochloride salt, said salt is then mixed with about 1 mole of EDC, about 1 mole of alkyl-leucine, in solution, DMF and diisopropylethylamine to form an β-amino-α-hydroxyamide reaction precursor. The α-hydroxy-amide is then separated and purified, by known means.

In an alternate embodiment, additional amino acids are substituted at the amino group of the β-amino-α-hydroxyamide, wherein the alkyloxycarbonyl can be cleaved from an alkyloxycarbonyl leucine substituent. Examples include cleaving a Boc group by reacting N,O-dimethylhydroxamate with about 4N HCL, which is in 1,4-dioxane, to form an amine hydrochloride salt. Additional N-substituted amino acid groups can then be substituted onto the amino group of the leucine substituent by following the aforementioned step for substitution of an amine hydrochloride salts with an alkyloxycarbonyl-leucine group.

In another embodiment, an amino acid ester is substituted for the hydroxyl of the carboxy group to form an α-hydroxyester. The β-L-amino-α-hydroxy-β-amino acid is mixed with a solution containing about 1 to 2 moles of thionyl chloride per mole of β-L-amino-α-hydroxy-β-amino acid, dissolved in methanol, to form a reaction mixture. In the reaction mixture, which is stirred at room temperature for an appropriate period, such as about 4 or more hours, the hydrogen from the carboxy group of the β-L-amino-α-hydroxy-β-amino acid is substituted with a methyl group to thereby form a methyl ester. The methyl ester is then separated and purified, by known means.

The amino group from the β carbon of the methyl ester is then substituted with a Cbz-Leu group, which is provided by a Cbz-Leu-hydroxysuccinimide ester (Cbz-Leu-OSu) solution in dioxane. The methyl ester is dissolved in THF and diisopropyl-ethylamine, and is then mixed with about 1 to 5 moles of Cbz-Leu-OSu, in solution, per mole of methyl ester. The reaction mixture is stirred for a suitable period, for example, about 6 to 12 hours to form an N-substituted methyl ester, which is then washed and crystallized, by known means.

The N-substituted methyl ester is subsequently dissolved in methanol and then saponified by being contacted with about 1 N NaOH to form a sodium salt of a carboxylic acid. The sodium salt of the carboxylic acid is then dissolved in water, washed with diethyl ether, and acidified with sodium bisulfate to a pH of about 2.0 to protonate the carboxy group and form a CBz-Leu-β-L-amino-α-hydroxy-β-amino acid. The CBz-Leu-β-L-amino-α-hydroxy-β-amino acid is extracted and crystallized, by known means, and is dissolved and then coupled with a second amino acid by substituting the hydroxyl from the carboxy group (—C(O)OH) of CBz-Leu-β-L-amino-α-hydroxy-β-amino acid.

Each mole of Cbz-Leu-β-amino-α-hydroxy-β-amino acid is combined with about 0.3 to 1 moles of HOBT in DMF, about 1 to 2 moles of EDC, about 1 to 2 moles of DIEA solution, and about 1 to 2 moles of a salt of the second amino acid to form a β-amino-α-hydroxyamide reaction precursor. The β-amino-α-hydroxyamide is then separated and purified, by known means.

In yet another embodiment, a β-amino-α-hydroxyamide is formed which contains a sulfide that can be oxidized to form a sulfone. The α-hydroxy-β-amino acid is dissolved in aqueous sodium bicarbonate and mixed with about 1 to 2 moles of an appropriate alkyloxycarbonyl-Leu-OSu, such as Cbz-Leu-OSu, which is dissolved in dioxane, per mole of α-hydroxy-β-amino acid. The amino group from the β carbon of the α-hydroxy-β-amino acid is then substituted with an alkyloxycarbonyl-Leu group. The alkyloxycarbonyl-Leu-α-hydroxy-β-amino acid is then separated and purified, by known means, and subsequently reacted with a suitable alkylthio-alkylamine to thereby substitute the hydroxyl of the carboxy group with an alkylthio-alkylamine group. Examples of suitable alkylthio-alkylamines include, for example, 2-(ethylthio)-ethylamine.

Each mole of alkyloxycarbonyl-Leu-α-hydroxy-β-amino acid is combined with about 1 to 5 moles of HOBT in N-methylpyrrolidinone, about 1 to 3 moles of ethyldimethylaminopropyl-carbodiimide, about 4 to 10 moles of diisopropylethylamine solution, and about 1 to 2 moles of an alkylthio-alkylamine to form an β-amino-α-hydroxyamide reaction precursor. The β-amino-α-hydroxyamide is then separated and purified, by known means.

The invention will be further illustrated by the following non-limiting examples.

EXEMPLIFICATION

Example I—Cbz-L-Leu-L-Abu-CONH-Et

Boc-protected L-aminobutyric acid (115.0 mmol) was coupled to N,O-dimethylhydroxylamine·HCl (12.2 g, 126.5 mmol) by the following procedure. The Boc-L-aminobutyric acid was dissolved in 200 mL of anhydrous tetrahydrofuran (THF) and placed under argon. 1,1'-carbonyldiimidazole (22.4 g, 138 mmole) was then added portionwise and the solution was stirred for 30 minutes under argon. N,O-dimethylhydroxylamine·HCl was dissolved in 75 mL dimethylformamide (DMF) with 21 mL diisopropylethylamine (DIEA) (15.6 g, 120 mmol) and added to the Boc-L-aminobutyric acid solution. The reaction mixture was allowed to stir overnight at room temperature. The reaction mixture was then concentrated in vacuo and diluted into ethyl acetate (300 mL) and washed with 1N HCl (3×100 mL), saturated aqueous sodium bicarbonate (3×100 mL), and saturated sodium chloride (1×100 mL). The organic phase was dried with magnesium sulfate, suction filtered and the filtrate concentrated in vacuo to a clear viscous oil which was dried overnight in vacuo. Mass spectral analysis of this oil found $(M+H)^+=247$. Yield=82%.

The Boc-L-aminobutyric N,O-dimethylhydroxamate was reduced to the aldehyde by the following procedure. Said hydroxamate (84.5 mmole) was dissolved in 125 mL anhydrous ethyl ether. LAH (3.5 g, 92 mmol) was added to 125 mL anhydrous ethyl ether and chilled (ice bath) in a round-bottom flask equipped with a pressure equalizing dropping funnel and thermometer. The hydroxamate was added to a dropping funnel, placed under argon, and added to the LAH suspension at a rate in which the temperature was not allowed to exceed 5° C. After all the hydroxamate was added, the reaction mixture was stirred for 30 minutes, and then ethyl acetate (50 mL) was added dropwise to destroy remaining excess LAH. 1N HCl (50 mL) was then added dropwise to dissociate the complex while the temperature was maintained at less than 5° C. The mixture was transferred to a separatory funnel and washed with 1N HCl (3×100 mL), saturated aqueous sodium bicarbonate (3×100 mL), and saturated sodium chloride (1×100 mL). The organic phase was dried with magnesium sulfate, suction filtered and the filtrate concentrated in vacuo to a clear viscous oil. Mass spectral analysis of this oil found $(M+H)^+=188$. Yield=85%.

The aldehyde (67 mmole) was converted to α-hydroxy-β-amino pentanoic acid by the following procedure. The aldehyde was dissolved in 100 mL methanol and chilled to 5° C. Sodium bisulfite (7.0 g, 67 mmol) was dissolved in 150 mL deionized water and chilled to 5° C. before addition to the aldehyde solution. This mixture was stirred overnight at 5° C. NaCN (4.0 g. 81 mmol) was dissolved in 100 mL deionized water and added with 300 mL ethyl acetate to the above solution. The reaction mixture was stirred for 5 hours at room temperature. The organic and aqueous layer were allowed to separate in a separatory funnel. The organic layer was collected, dried with magnesium sulfate, suction filtered and the filtrate concentrated in vacuo to a clear, colorless, viscous syrup. The cyanohydrin (47 mmol) was dissolved in 250 mL 1,4 dioxane, 250 mL concentrated HCl, and 10 mL anisole and the solution gently refluxed, with stirring, overnight.

The hydrolysis reaction was allowed to cool to room temperature and then dried in vacuo to a brown paste. The residue was dissolved in 100 mL deionized water and washed with ethyl ether (3×50 mL). The aqueous phase was then placed on a Dowex 50×8 (100–200 mesh, H+ form) column (25×1.8 cm). The column was washed with deionized water until the pH was neutral and then eluted with 2M ammonium hydroxide (approx. 1.5 L). The eluant was dried in vacuo to yield a tan amorphous solid. Mass spectral analysis of this solid found $(M+H)^+=134$. Yield=65%.

The α-hydroxy-β-amino pentanoic acid was converted to the Boc-protected hydroxy ethyl amide by the following procedure. The α-hydroxy-β-amino pentanoic acid (7.2 mmol) was dissolved in 1N NaOH (9 mL). To the solution was added a solution of di-tert-butyl dicarbonate (1.6 g, 7.3 mmol) in dioxane (9 mL). The reaction mixture was stirred at room temperature and the pH maintained greater than 10 with 1N NaOH. After four hours the reaction was diluted into deionized water (80 mL) and washed with ethyl ether (2×25 mL). The aqueous phase was chilled in an ice bath and acidified to pH 2 with 1N HCl. This mixture was extracted with ethyl ether (3×30 mL). The organic phase was dried with magnesium sulfate, suction filtered and the filtrate concentrated in vacuo to a clear colorless oil. Mass spectral analysis of this oil found (M+H)$^+$=234. Yield=63%.

The N-Boc-α-hydroxy-β-amino pentanoic acid (5.7 mmol) was dissolved in 12 mL of 0.5M HOBT in DMF and placed in an ice bath. Ethyl-dimethylaminopropylcarbodiimide (1.2 g, 6.25 mmol) was added followed by 70% ethylamine solution (800 uL, 9.9 mmol). The solution was stirred overnight. The solution was dissolved in ethyl acetate (50 mL) and washed with 1N HCl (3×50 mL), saturated aqueous sodium bicarbonate (3×50 mL) and saturated sodium chloride (1×50 mL). The organic phase was dried with magnesium sulfate, suction filtered and the filtrate concentrated in vacuo to an off white solid. Mass spectral analysis of this oil found (M+H)$^+$=261. Yield=66%.

The Boc-hydroxy ethyl amide (4 mmol) was dissolved in 4N HCl/dioxane (10 mL, 40 mmol HCl) and stirred for 30 minutes. The white semi-solid reaction mixture was dried in vacuo to yield the α-hydroxy-β-amino acid ethylamide hydrochloride salt in a quantitative yield. The amine hydrochloride salt (10.4 mmol) was coupled to Cbz-Leu (3.0 g, 11.3 mmol) by the following procedure. The Cbz-Leu was dissolved in 1M HOBt in N-methylpyrrolidinone (11.3 mL, 11.3 mmol 1-hydroxybenzotriazole) and added to a flask containing EDC (2.2 g, 11.5 mmol), DMF (10 mL) and DIEA (2 mL), and the reaction was stirred overnight at room temperature. The reaction solution was diluted into ethyl acetate (150 mL) and the resulting milky mixture was washed with 1N HCl (3×50 mL), saturated aqueous sodium bicarbonate (3×50 mL) and saturated aqueous sodium chloride (1×50 mL). The organic phase was dried with anhydrous magnesium sulfate, suction filtered and the filtrate was concentrated to a viscous syrup on a rotary evaporator. This was dried in vacuo to a brittle foam which was redissolved in the minimum amount of ethyl ether and allowed to crystallize in an ice bath. The solid was isolated by suction filtration, washed with cold ethyl ether and dried in vacuo. Mass spectral analysis of this solid found (M+H)$^+$=408. Yield=70%.

The β-amino-α-hydroxyamide was oxidized to the α-ketoamide by the following procedure. In a 25 mL round bottom flask was placed TEMPO (5 mg), potassium bromide (25 mg), water (0.11 mL) and methylene chloride (5 mL). As this mixture was stirred, the β-amino-α-hydroxyamide (2.13 mmol) was added and the reaction was stirred in an ice bath until the hydroxyamide was dissolved. To a 5.25% sodium hypochlorite solution (commercial bleach, 25 mL) was added sodium bicarbonate (300 mg) and this was stirred until the solid was dissolved. Over a period of approximately 5 minutes, 3.4 mL of this solution was added with vigorous stirring to the above reaction mixture in an ice bath. The reaction mixture became a solid mass requiring the addition of 5 to 10 mL methylene chloride to obtain a slurry. After 20 min. another portion of TEMPO (5 mg) was added and more bleach solution was added as above. When the addition was complete, TLC showed no starting material remaining. The reaction was diluted into ethyl acetate (100 mL) and washed with 0.5N HCl (3×30 mL), saturated sodium bicarbonate (3×30 mL) and saturated sodium chloride (1×30 mL). The organic phase was dried with anhydrous magnesium sulfate, suction filtered and concentrated in vacuo to a white solid. This solid was vigorously stirred with ethyl ether (approx. 10 mL) and then isolated by suction filtration. Mass spectral analysis of this oil found (M+H)$^+$=406. Elemental analysis for $C_{21}H_{31}N_3O_5$ found 61.96 C, 7.77 H and 10.07 N while calculated values were 62.20 C, 7.71 H and 10.36 N. For $^1$HNMR (500 MHz, d6-DMSO) analysis, the shifts observed were 0.84–0.93(m,9H); 1.04(t,3H); 1.43(t,2H); 1.45–1.65(m,2H); 1.80(m,1H); 3.15(q,2H); 4.1 (q,1H); 4.87(m,1H), 5.05(s,2H); 7.30–7.45(m,5H); 8.23(d,1H); 8.67(t,1H). Yield=50%.

Example II—Cbz-L-Leu-L-Norvaline-CONH-Et

Cbz-L-Leu-L-Norvaline-CONH-Et was synthesized according to the procedure of Example I. Mass spectral analysis of intermediary compounds found:

Boc-L-norvaline hydroxamate (M+H)$^+$=261 (Yield=86%),

Boc-L-norvalinal (M+H)$^+$=202 (Yield=90%),

α-hydroxy-β-amino-hexanoic acid (M+H)$^+$=147 (Yield=61%),

N-Boc-α-hydroxy-β-amino-hexanoic acid (M+H)$^+$=248 (Yield=46% ),

Boc-α-hydroxy ethyl amide (M+H)$^+$=275 (Yield=66% );

Cbz-L-Leu-α-hydroxyethylamide (M+H)$^+$=422 (Yield=67%).

Analyses of the final product provided the following results: Mass spectral analysis found (M+H)+=420. Elemental analysis for $C_{22}H_{33}N_3O_5$ found 62.87 C, 7.97 H and 9.92 N while calculated values were 62.99 C, 7.93 H and 10.02 N. For $^1$HNMR (500 MHz, d6-DMSO) analysis, the shifts observed were 0.87(q,9H); 1.04(t,3H); 1.40(m,5H); 3.15(m, 2H); 4.10(q,1H); 4.95(m,1H); 5.01(s,2H); 7.0–7.39 (m,5H); 8.23(d,1H); 8.69(t,1H). $R_f$=0.34 (20:1, DCM:MeOH). Yield=67%.

Example III—Cbz-L-Leu-L-Phenylalanine-CONH-Et

Cbz-L-Leu-L-Phenylalanine-CONH-Et was synthesized according to the procedure of Example I. Mass spectral analysis of intermediary compounds found:

Boc-L-phenylalanine hydroxamate (M+H)$^+$=309 (Yield=99% ),

Boc-L-phenylalinal (M+H)$^+$=250 (Yield=99%),

α-hydroxy-β-amino-γ-phenyl-butanoic acid (M+H)$^+$=196 (Yield=52% ),

N-Boc-α-hydroxy-β-L-amino-γ-phenyl-butyric acid (M+H)$^+$=296 (Yield=79%),

N-Boc-α-hydroxy-α-amino-γ-phenylbutyric acid (M+H)$^+$=323 (Yield=86%);

Cbz-L-Leu-α-hydroxy-α-amino-γ-phenylbutyric acid (M+H)$^+$=470 (Yield=83%).

Analyses of the final product provided the following results: Mass spectral analysis found (M+H)$^+$=468. Elemental analysis for $C_{26}H_{33}N_3O_5$ found 66.39 C, 7.06 H and 8.88 N while calculated values were 66.67 C, 7.11 H and 8.99 N. For $^1$HNMR (500 MHz, d6-DMSO) analysis, the shifts observed were 0.85(q,6H); 1.03(t,3H); 1.36(m,2H); 1.57(m, 1H); 2.83(dd,1H); 3.12(m,2H); 4.07(q,1H); 5.07(m,2H); 5.20(m,1H); 7.25(m,5H); 7.4(m,5H); 8.30(d,1H); 8.70(t, 1H). Yield=75%.

Example IV—Cbz-L-Leu-D-Phe-CONH-Et

Cbz-L-Leu-D-Phe-CONH-Et was synthesized according to the procedure of Example I. Analyses of the final product provided the following results: Mass spectral analysis found (M+H)$^+$=468. Elemental analysis for $C_{26}H_{32}N_3O_5$ found 66.76 C, 7.20 H and 8.87 N while calculated values were 66.69 C, 7.11 H and 8.99 N. For $^1$HNMR (500 MHz, d6-DMSO) analysis, the shifts observed were 0.77(q,6H);

1.05(t,3H); 1.15(m,2H); 1.39(m,1H); 2.72(q,1H); 3.15(m, 3H); 4.05(m,1H); 4.99(q,2H); 5.19(m,1H); 7.22(m,5H); 7.34(m,5H); 8.30(d,1H); 8.70(t,1H). Yield=84%.

Example V—Cbz-L-Leu-L-Phe-C(O)-Phe-OMe

The α-hydroxy-β-amino acid (3(S)-amino-2(R,S)-hydroxy-4-phenyl butanoic acid) was converted to the methyl ester by the following procedure. Methanol (40 mL) was chilled in an ice bath and to this was carefully added thionyl chloride (5.0 mL, 68.5 mmol). When the addition was complete the α-hydroxy-β-amino acid (4.0 g, 17.3 mmol) was added and the stoppered flask allowed to come to room temperature. The reaction was stirred overnight. The solution was then diluted into methanol and twice rotary evaporated to dryness. The glassy foam was redissolved in a minimum amount of methanol which crystallized upon addition of diethyl ether. A white crystalline solid was isolated by suction filtration washed with cold ether and dried in vacuo. TLC (Butanol:Acetic Acid: water, 4:1:1) found Rf=0.59. Mass spectral analysis of this solid found $(M+H)^+=210$.

The methyl ester was coupled to Cbz-Leu-OSu by the following procedure. Methyl (3(S)-amino-2(R,S)-hydroxy-4-phenyl butanoic acid) hydrochloride salt (1.75 g, 7.14 mmol) was dissolved in 20 mL THF with 2 equivalents of diisopropyl ethylamine (1.4 mL). Cbz-Leucine hydroxysuccinimide ester (3.2 g, 113.2 mmol, 1.25 eq) was dissolved in 20 mL dioxane and added to the solution of the methyl ester. The reaction was allowed to stir at room temperature overnight. The reaction mixture was diluted into ethyl acetate (100 mL) and washed with 1N HCl (3×80 mL), saturated aqueous sodium bicarbonate (3×80 mL), and saturated sodium chloride (1×80 mL). The organic phase was dried with magnesium sulfate, suction filtered and the filtrate concentrated on a rotary evaporator to an off white solid. The methyl ester was saponified without purification.

The ester (3.65 g, 7.9 mmol) was dissolved in methanol (16 mL) and to this was added 1N NaOH (16 mL). The reaction was stirred for one hour after which a white solid mass formed. This was dissolved in 100 mL water and washed with diethyl ether (3×50 mL). The aqueous phase was acidified with solid sodium bisulfate to ca. pH 2.0 and extracted with ethyl acetate (3×50 mL). The ethyl acetate layer was dried with anhydrous magnesium sulfate, suction filtered and dried on a rotary evaporator to a clear colorless glass. This material was recrystallized from a minimum amount of diethyl ether. TLC (chloroform: methanol:acetic acid 85:10:5) found diastereomers with $R_f$=0.42 & 0.32. Mass spectral analysis of this solid found (M+H+)=443. Yield=89.6%.

Cbz-Leu-3(S)-amino-2(R,S)-hydroxy-4-phenyl butanoic acid (Z-Leu-Phe-α-hydroxy acid) was coupled to L-Phe by the following procedure. Cbz-Leu-3(S)-amino-2(R,S)-hydroxy-4-phenyl butanoic acid (175.0 mg, 0.4 mmol) was dissolved in 0.5M HOBt in DMF (3.0 mL 1.5 mmol 1-hydroxybenzotriazole) and added to a flask containing EDC (120 mg, 6.3 mmol) and diisopropylethylamine (80 uL, 0.46 mmol). To this solution was added the L-Phe·HCl salt (1.05 eq.) and the stoppered flask was stirred at room temperature overnight.

The reaction solution was diluted into ethyl acetate (50 mL) and the resulting milky mixture was washed with 1N HCl (3×50 mL), saturated aqueous sodium bicarbonate (3×50 mL) and saturated aqueous sodium chloride (1×50 mL). The organic phase was dried with anhydrous magnesium sulfate, suction filtered and the filtrate was concentrated to a viscous syrup on a rotary evaporator. This was dried in vacuo to a brittle foam which was redissolved in the minimum amount of ethyl ether and allowed to crystallize in an ice bath. The solid was isolated by suction filtration, washed with cold ethyl ether and dried in vacuo. Mass spectral analysis of this oil found $(M+H)^+=433$. Yield=72%.

The alcohol was oxidized to the ketone by the following procedure. In a 25 mL round bottom flask was placed TEMPO (1 mg), potassium bromide (4 mg), water (0.016 mL) and methylene chloride (10 mL). As this mixture was stirred, the alcohol (0.31 mmol) was added and the reaction was stirred in an ice bath until the alcohol was dissolved. To a 5.25% sodium hypochlorite solution (commercial bleach, 25 mL) was added sodium bicarbonate (300 mg) and this was stirred until the solid was dissolved. Over a period of approx. 5 min., 1.0 mL of this bleach solution was added with vigorous stirring to the above reaction mixture in an ice bath. The reaction mixture became a solid mass requiring the addition of 5 to 10 mL methylene chloride to obtain a slurry. Over a period of 30 min., three portions of TEMPO (2 mg) and three portions of bleach solution (0.5 mL) were added as above. When the addition was complete, TLC showed no starting material remaining. The reaction was diluted into dichloromethane (70 mL) and washed with a solution of 1.6 g potassium iodide in 10% HCl (50 mL), 10% sodium thiosulfate (50 mL) and saturated sodium chloride (1×50 mL). The organic phase was dried with anhydrous magnesium sulfate, suction filtered and concentrated on a rotary evaporator to a white solid. This solid was recrystallized from ethyl acetate.

Analyses of the final product provided the following results: Mass spectral analysis found $(M+H)^+=602$ for $C_{34}H_{39}N_3O_7$. For $^1$HNMR (600 MHz, d6-DMSO) analysis, the shifts observed were 0.85(q,7H); 1.37(t,2H); 1.57(q,1H); 2.59(m,1H); 2.69(q,1H); 3.10(m,2H); 3.65(s,3H); 4.00 (q,1H); 4.64(m,1H); 4.90(q,2H); 5.16(m,1H); 7.25(m,15H); 8.19(d,1H); 9.13(d,1H). $R_f$=0.57, (20:1, DCM:MeOH).

Example VI—Cbz-L-Leu-L-Phe-C(O)-Tyr(O-t-butyl)-OMe

Cbz-L-Leu-L-Phe-C(O)-Tyr(O-t-butyl)-OMe was synthesized according to the procedure of Example V with the exception that in the case of the methyl ester of H-Tyr-(O-tert-butyl)-HCl, the ether group was removed after the oxidation by dissolving the compound in 95% trifluoroacetic acid/5% water (10 mL) and stirring for 20 minutes. This solution was dissolved in 50 ml dichloromethane, dried over anhydrous magnesium sulfate, suction filtered and dried on a rotary evaporator.

Mass spectral analysis of alcohol intermediate found $(M+H)^+=674$. Yield=73%. Analyses of the final product provided the following results: Mass spectral analysis found $(M+H)^+=618$ for $C_{34}H_{39}N_3O_8$. For $^1$HNMR (500 MHz, d6-DMSO) analysis, the shifts observed were 0.76 (m) and 0.82–0.90 (q,7H); 1.37(t,2H); 1.57(s,1H); 2.65(q,1H); 2.79(d,1H); 2.89(q,1H); 3.00(q,1H); 3.63(s,3H); 4.00(q, 1H); 4.53(s,1H); 4.90(m,2H); 5.1(m,1H); 6.65(d,2H); 6.9–7.3(m,12H); 8.20(d,1H); 9.00(d,1H); 9.21(s,1H). $R_f$=0.40 (20:1, DCM:MeOH).

Example VII—Cbz-L-Leu-L-Phe-C(O)-L-α-Abu-OMe

Cbz-L-Leu-L-Phe-C(O)-L-α-Abu-OMe was synthesized according to the procedure of Example V.

Mass spectral analysis of alcohol intermediate found (M+H)⁺=542. Yield=75%. Analyses of the final product provided the following results: Mass spectral analysis found (M+H)⁺=540 for $C_{29}H_{37}N_3O_7$. For ¹HNMR (600 MHz, d6-DMSO) analysis, the shifts observed were 0.85(q,10H); 1.37(m,2H); 1.58(m,1H); 1.69–1.84(m,2H); 2.85(q,1H); 3.08(q,1H); 3.63(s,3H); 4.00(q,1H); 4.18(m,1H); 5.00(q, 2H); 5.20(m,1H); 7.19–7.37(m,10H); 8.30(d,1H); 9.00(d, 1H). $R_f$=0.40 (20:1, DCM:MeOH).

Example VIII—Cbz-L-Leu-L-Phe-C(O)-L-Norleucine-OMe

Cbz-L-Leu-L-Phe-C(O)-L-Norleucine-OMe was synthesized according to the procedure of Example V. Mass spectral analysis of alcohol intermediate found (M+H)⁺= 570. Yield=75%. Analyses of the final product provided the following results: $R_f$=0.31 (20:1, DCM:MeOH)

Example IX—Cbz-L-Leu-L-Phe-C(O)-L-Ala-OMe

Cbz-L-Leu-L-Phe-C(O)-L-Ala-OMe was synthesized according to the procedure of Example V. Mass spectral analysis of alcohol intermediate found (M+H)⁺=528. Yield= 81%. Analyses of the final product provided the following results: Mass spectral analysis found (M+H)⁺=526. Elemental analysis for $C_{28}H_{35}N_3O_7$ found 63.12 C, 6.51 H and 7.90 N while calculated values were 63.98 C, 6.71 H and 7.90 N. For ¹HNMR (600 MHz, d6-DMSO) analysis, the shifts observed were 0.80–0.90(q,6H); 1.33(d) and 1.37(t,5H); 1.57(m,1H); 2.83(q,1H); 3.10(q,1H); 3.35(s, 4H); 3.65(s, 3H); 4.05(q,1H); 4.35(m,1H); 5.00(q,2H); 5.25 (m,1H); 7.20–7.40(m,10H); 8.3(d,1H); 9.1(d,1H).

Example X—Cbz-L-Leu-L-Phe-C(O)-L-Ala-OH

Cbz-L-Leu-L-Phe-C(O)-L-Ala-OH was synthesized according to the procedure of Example V. Analyses of the final product provided the following results: Mass spectral analysis found (M+H+)=512. $R_f$=0.31 (20:1, DCM:MeOH).

Example XI—Cbz-L-Leu-L-Abu-C(O)—NH—(CH₂)₂—SO₂—Et

The α-hydroxy-β-amino acid was synthesized as described in Example I and was then converted to Cbz-Leu-α-hydroxy-β-L-amino pentanoic acid by the following procedure. The α-hydroxy-β-amino acid (19.4 mmol) was dissolved in saturated aqueous sodium bicarbonate (40 mL). To this solution was added a solution of Cbz-Leu-ONSu (8.8 g, 24.3 mmol) in dioxane (20 mL). The reaction was stirred at room temperature overnight. The solution was concentrated in vacuo, and the residue dissolved in ethyl acetate (100 mL) and washed with 1N HCl (3×50 mL) followed by saturated aqueous sodium chloride (1×50 mL). The organic phase was dried with anhydrous magnesium sulfate, suction filtered and the filtrate concentrated in vacuo to an off-white semi-solid. This material was purified by silica gel column chromatography.

Cbz-Leu-Abu-α-hydroxy-β-amino acid was converted to the hydroxy (ethylthio)-ethyl amide by the following procedure. The 2-(ethylthio)-ethylamine hydrochloride (38 mg, 0.263 mmol) was dissolved in 0.145 mL of 1M HOBT in N-methylpyrrolidinone. Diisopropylethylamine (0.114 mL, 0.657 mmol) was added, followed by the Cbz-protected-Leu-Abu-α-hydroxy-β-amino acid (50 mg, 0.131 mmol). Ethyl-dimethylaminopropyl-carbodiimide (52 mg, 0.263 mmol) was added and the solution was stirred overnight. Another 26 mg (0.263 mmol) of ethyldimethylaminopropylcarbodiimide was added and the solution was again stirred overnight. The solution was concentrated in vacuo, the residue dissolved in ethyl acetate (25 mL) and washed with 1N HCl (2×50 mL), saturated aqueous sodium bicarbonate (2×50 mL), and saturated sodium chloride (1×50 mL). The organic phase was dried with anhydrous magnesium sulfate, suction filtered and the filtrate concentrated in vacuo to an off white solid. Mass spectral analyses of the solid found (M+H⁺)=468.

The β-amino-α-hydroxyamide was oxidized to the α-ketoamide by the following procedure. The β-amino-α-hydroxyamide (41 mg, 0.088 mmol) was dissolved in methylene chloride (5 mL). TEMPO (2 mg), potassium bromide (3 mg) and water (0.05 mL) were added. The reaction was stirred in an ice bath for 15 minutes. To a 5.25% sodium hypochlorite solution (5.25% NaOCl, 25 mL) was added sodium bicarbonate (300 mg) and this mixture was stirred until the solid was dissolved. Over a period of approx. 5 min. 1.21 mL of this solution was added with vigorous stirring to the reaction mixture in an ice bath. The reaction mixture was then stirred for 2 hours, with periodic addition of ice to the bath. After 2 hours, TLC showed no starting material remaining. The layers were separated and the aqueous layer extracted with methylene chloride (1×5 mL). The combined organic layer was washed with 0.1M NaI in 10% HCl (1×10 mL), 10% aq. sodium thiosulfate (1×10 mL) and saturated sodium chloride (1×10 mL). The organic phase was dried with anhydrous magnesium sulfate, filtered and concentrated in vacuo to a white solid. This solid was vigorously mixed with ethyl ether (approx. 10 mL) and then isolated by decanting the solvent to obtain 18 mg solid. This material was further purified by preparative reverse-phase HPLC on a $C_4$ column to yield 7.7 mg (0.015 mmol) of Cbz-Leu-α-Keto-β-L-amino pentanoic acid 2-ethylsulfonyl ethylamide as a white solid. Analyses of the final product provided the following results: Mass spectral analysis found FAB-MS m/e 498 (M+H)⁺. For ¹HNMR (600 MHz, d6-DMSO) analysis, the shifts observed were 0.88(m,9H), 1.20(t, J=7.5 Hz, 3H), 1.41(m,3H), 1.58(m,2H), 1.80 (m,1H), 3.12(q, J=7.5 Hz, 2H), 3.52(m,2H), 4.10 (dt, J=8.4 Hz, 0.5H), 4.87(m,1H), 5.02(s,2H), 7.35(m,5H), 7.40(d, J=8.4 Hz, 1H), 8.28(d, J=6.6 Hz, 1H), 8.85(t, J=5.6 Hz, 1H). $R_f$=0.32 (methylene chloride:methanol, 20:1).

Example XII—Morpholinourea-L-Leu-L-Abu-CONH-Et

Ten grams of N-Boc-Abu was dissolved in 100 ml of anhydrous THF. To this solution was added 9.4 mL of diisopropylethylamine and 25.61 g (49.2 mmoles) of PyBOP. The solution was allowed to equilibrate for 10 minutes. Following equilibration, a solution of 5.28 g (54.1 mmoles) of N,O-dimethylhydroxylamine hydrochloride dissolved in 5 mL of acetonitrile and containing 25.6 mL of N,N-diisopropylethylamine (54.1 mmoles) was added. The reaction was stirred overnight at room temperature.

The reaction mixture was then concentrated in vacuo and redissolved in 200 mL of ethyl acetate. The ethyl acetate layer was washed three times with 1.0N HCl (100 mL), three times with saturated sodium bicarbonate (100 mL) and three times with brine (100 mL). The reaction mixture was dried over magnesium sulfate, filtered and concentrated in vacuo giving a yellow oil. The crude product was purified by silica gel chromatography using 2:1 ethyl acetate:hexane as the eluent. The product was isolated as a white solid (77% yield)

with an Rf of 0.77 on silica employing the same solvent system used above.

Anhydrous ethyl ether (75 mL) and 0.9 g (23.7 mmoles) of lithium aluminum hydride were placed in a 500 mL round-bottomed flask. The suspension was cooled in an ice bath for ten minutes. A pressure equalizing dropping funnel, containing 4.5 g (18.4 mmoles) of Boc-Abu hydroxamate dissolved in 75 mL of anhydrous ethyl ether, was attached to the round bottom flask and the contents were added dropwise over one hour, with continued cooling. The reaction mixture was allowed to react for an additional two hours at room temperature.

The reaction mixture was then cooled in an ice bath and a cold solution of potassium hydrogen sulfate (5.4 g in 230 mL of water) was slowly added to the reaction flask and allowed to react for an additional 10 minutes. The aqueous and organic layers were separated and the aqueous layer was extracted with anhydrous ethyl ether (3×100 mLs). The combined organic layer was washed 3×100 mLs each with 1.0N HCl, saturated sodium bicarbonate and brine and then dried over magnesium sulfate, filtered and concentrated in vacuo. The product was isolated as a white solid (63% yield), with an Rf of 0.90 on silica, using 2:1 ethyl acetate:hexane as the eluent.

N-Boc abuinal (4.00 g (21.39 mmoles)) was dissolved in 26 mL of methanol and cooled on ice. To this was added a cold solution of 2.67 g of sodium bisulfite dissolved in 54 mL of water. This reaction was stirred overnight at 4° C. 265 mL of ethyl acetate was then added to the above reaction mix followed by a solution of 1.08 g (22 mmoles) of sodium cyanide dissolved in 80 mL of water, and then stirred overnight at 4° C. The aqueous and organic layers were separated and the aqueous layer was extracted twice with 50 mL of ethyl acetate. The combined organics were dried over magnesium sulfate, filtered and evaporated in vacuo leaving a clear colorless oil (70% yield). TLC analysis on silica using 1:1 ethyl acetate:hexane as the eluent showed the product to have an Rf of 0.69. The Boc-Abu cyanohydrin was used without further purification.

The Boc-Abu cyanohydrin isolated was dissolved in 120 mL of 4N HCl/dioxane. 60 mL of water was then added to the reaction mixture and it was refluxed overnight. The reaction mixture was rotavapped to dryness leaving a brown solid. The solid was dissolved in water and extracted three times with 100 mL of ethyl acetate. The aqueous layer was then concentrated in vacuo and rotavapped from ethyl ether three times. This material was used without further purification.

α-Hydroxy-β-L-amino pentanoic acid (2.9 g (17.16 mmoles)) was dissolved in 51 mL of 2:1 dioxane:water and placed in an ice bath. To this was added 42.5 mL (42.5 mmoles) of 1N sodium hydroxide. The reaction was allowed to cool and 6.12 g (28.04 mmoles) of di-tert-butyl dicarbonate was then added. The pH of the reaction was maintained between 9.5 and 10 by the addition of base. Following an overnight reaction time it was worked up as follows. The dioxane was rotavapped off and an additional 15 mL of water was added to the reaction mixture. The water was covered with a layer of ethyl acetate and cooled on ice. The pH of the aqueous layer was adjusted to 2.5 with 3N HCl. The organic and aqueous layers were separated and the aqueous layer was extracted twice with 50 mL of ethyl acetate. The combined organic layers were dried over magnesium sulfate, filtered, and evaporated in vacuo leaving a brown viscous oil. The crude material was purified by silica gel chromatography using 91:8:1 chloroform:methanol:acetic acid as the eluent. There remained 1.140 g Boc-α-hydroxy-β-amino pentanoic acid (26.3% yield from Boc-Abuinal). TLC analysis on silica using the same system detailed above showed the product to be one spot with an Rf value of 0.22.

Boc-α-hydroxy-β-amino pentanoic acid (0.96 g (4.13 mmoles)) was dissolved in 35 mL of dimethylformamide (DMF) and cooled in an ice bath. 0.78 mL (12.4 mmoles) of 70% triethylamine and 0.84 g (6.2 moles) of 1-hydroxybenzotriazole (HOBT) were added and allowed to equilibrate for thirty minutes. After this time 1.0 g (5.22 mmoles) of 1-(3-dimethylaminopropy)-3-ethylcarbodiimide hydrochloride (EDC) suspended in 10 mL of DMF was added. The reaction was allowed react at room temperature overnight.

The reaction was then rotavapped to dryness and redissolved in 100 mL of chloroform and washed three times with 35 ml of saturated sodium bicarbonate and then brine. The mixture was dried over magnesium sulfate, filtered and concentrated in vacuo. The crude material was purified by silica gel column chromatography employing 9:1 ethyl acetate:hexane. 0.938 g (85% yield) of product was isolated which possessed and Rf value of 0.55 in the above solvent system.

Boc-α-hydroxy-β-amino pentanoic acid ethylamide (0.233 g, 0.894 mmoles) was dissolved in 5 mL of dioxane followed by the addition of 20 mL of 4N HCl/dioxane. The reaction mixture was allowed to react for two hours. After this time, the reaction mixture was concentrated in vacuo and used immediately in the next step.

L-Leucine (1.31 g (10 mmoles)) was placed in a 3-neck round-bottom flask, equipped with two pressure equalizing dropping funnels. 12.5 mL of 1.0N NaOH (12.5 mmoles) was added to the flask and then the mixture was cooled on ice. 12.5 mL of 1.0N NaOH was placed in one dropping funnel and 1.46 mL (12.5 mmoles) of morpholinocarbonyl chloride was placed in the other. The contents of the addition funnels were added to the flask simultaneously over ten minutes. The mixture was allowed to react for an additional twenty minutes. The reaction mixture was then washed twice with 15 mL of ethyl acetate. The aqueous layer was cooled on ice and acidified to a pH of 2 with 1.0N HCl. The aqueous layer was extracted three times with 15 mL of ethyl acetate. The combined organics were dried over magnesium sulfate, filtered and concentrated in vacuo. There remained 0.48 g of a white solid (20% yield) which possessed an Rf value of 0.45 using 91:8:1 chloroform:methanol:acetic acid as the eluent.

Boc-α-hydroxy-β-amino pentanoic acid ethylamide (0.266 g, was dissolved in 5 mL of dioxane followed by the addition of 20 mL of 4N HCl/dioxane. The reaction mixture was allowed to react for two hours. After this time, the reaction mixture was concentrated in vacuo and used immediately in the next step. The Boc-α-hydroxy-β-amino pentanoic acid ethylamide·HCl was dissolved in 30 mL of anhydrous DMF and cooled on an ice bath for ten minutes. To this solution was added 0.30 g (1.23 mmoles) of morpholinoleucine urea, 0.55 mL (3.07 mmoles) of diisopropylethylamine and 0.152 g (1.13 moles) of 1-hydroxybenzotriazole and allowed to equilibrate for thirty minutes. After this time, 0.218 g (21.13 mmoles) of EDC suspended in 10 mL anhydrous DMF was added and the reaction mixture was allowed to react overnight. The reaction mixture was concentrated in vacuo and the resulting residue was purified by silica gel column chromatography employing 90:10 chloroform:methanol as the eluent. There remained 0.2414 g (61.04% yield) of a white solid with an Rf value of 0.36 in the solvent system detailed above.

Morpholinourea-L-Leu-α-hydroxy-β-L-amino pentanoic acid ethylamide (0.1225 g (0.317 mmoles)) was dissolved in 10 mL of methylene chloride and cooled in an ice bath. To this mixture was added 0.5 mg (0.00317 mmoles) of 2,2,6, 6-tetramethyl-1-piperidinyloxy, free radical (TEMPO) and 0.0159 mL (0.0317 mmoles) of an aqueous KBr solution (5.95 g of KBr dissolved in 25 mL of water). The reaction mix was stirred vigorously while four 87 microliter portions of a 1M aqueous sodium hypochlorite (pH 9.5) were added at 15 minute intervals. After this time the reaction mixture was analyzed by TLC employing 90:10 chloroform:methanol to check for completeness of the reaction. If the reaction was not complete another portion of TEMPO and another regimen of the sodium hypochlorite solution should be added. This reaction required three additional regimens of TEMPO and sodium hypochlorite.

When the reaction was deemed complete by TLC, the layers were separated. The aqueous layer was extracted with methylene chloride (3×10 mL). The combined organic layer was washed with 10% HCl (1×10 mL), 30 mL of a 100 mL stock solution of 10% HCl containing 1.6 g of KI, 10% sodium thiosulfate (2×30 mL) and brine (1×30 mL). The organic layer was then dried over magnesium sulfate, filtered and concentrated in vacuo. The crude material was triturated with petroleum ether to give an off-white solid which was recrystallized from ethyl acetate hexane. There remained 0.048 g (39.6% yield) of a white solid with an Rf value of 0.32 in the solvent system detailed above.

TLC analysis of the product on silica gel gave an Rf value of 0.32 in the solvent system detailed above. HPLC analysis was performed on a Vydac C4 column (4.6×250 mm) at 60° C. using a gradient of 15–25% B/30 minutes (A=0.1% TFA in water, B=0.1% TFA in acetonitrile). The product had a retention time of 14 minutes and a purity of 97.8%. Analyses of the final product provided the following results: Mass spectral analysis (FABMS) found (M+H)$^+$ at m/z 385. Elemental analysis for $C_{18}H_{32}N_4O_5$ found 56.14 C, 8.24 H and 14.36 N while calculated values were 56.23 C, 8.39 H and 14.57 N. For $^1$HNMR (600MHz, d6-DMSO) analysis, the shifts observed were 8.65(t,1H), 8.10(d,1H), 6.41(d,1H), 4.85(m,1H), 4.20(m,1H), 3.51(m,4H), 3.26(m,4H), 3.12(m,2H), 1.75(m,1H), 1.62(m,1H), 1.48(m,2H), 1.40(m,1H), 1.02(t,3H), 0.85(m,9H).

Example
XIII—Dimethylurea-L-Leu-L-Abu-CONH-Et

Dimethylurea-L-Leu-L-Abu-CONH-Et was synthesized generally according to the procedure of Example XII with the exception of the synthesis of the reactant dimethylurea-L-Leu-L-Abu hydroxy ethyl amide.

L-Leucine (1.31 g (10 mmoles)) was placed in a 3 neck round-bottomed flask, equipped with two pressure equalizing dropping funnels. 12.5 mL of 1.0N NaOH (12.5 mmoles) was added to the flask and then the mixture was cooled on ice, 12.5 mL of 1.0N NaOH was placed in one dropping funnel and 1.15 mL (12.5 mmoles) of dimethylcarbamoyl chloride was placed in the other. The contents of the addition funnels were added to the flask simultaneously over ten minutes. The mixture was allowed to react for an additional fifteen minutes. The reaction was then washed twice with 15 mL of ethyl acetate. The aqueous layer was cooled on ice and acidified to a pH of 2 with 1.0N HCl. The aqueous layer was extracted three times with 15 mL of ethyl acetate. The combined organics were dried over magnesium sulfate, filtered and concentrated in vacuo. There remained 0.10 g of a white solid (5%) which possessed an Rf value of 0.31 using 91:8:1 chloroform:methanol:acetic acid as the eluent.

Boc-α-hydroxy-β-L-amino pentanoic acid ethylamide (0.233 g, 0.894 mmoles) was dissolved in 5 mL of dioxane followed by the addition of 20 mL of 4N HCl/dioxane. The reaction mixture was allowed to react for two hours. After this time, the reaction mixture was concentrated in vacuo and used immediately in the next step. The α-hydroxy-β-L-amino pentanoic acid ethylamide HCl salt was dissolved in 30 mL of anhydrous DMF and cooled on an ice bath for ten minutes. To this solution was added 0.217 g (1.07 mmoles) of morpholinoleucine urea, 0.46 mL (2.68 mmoles) of diisopropylethylamine and 0.133 g (0.984 mmoles) of 1-hydroxybenzotriazole (HOBt) and allowed to equilibrate for thirty minutes. After this time, 0.188 g (0.984 mmoles) of EDC suspended in 10 mL of anhydrous DMF was added and the reaction mixture was allowed to react overnight. The reaction mixture was concentrated in vacuo and the resulting residue was purified by silica gel column chromatography employing 90:10 chloroform:methanol as the eluent. There remained 0.2044 g (66.56% yield) of a white solid with Rf value of 0.38 in the solvent system detailed above.

0.100 g (0.291 mmoles) of Dimethylurea-Leu-α-hydroxy-β-amino pentanoic acid ethyl amide was dissolved in 10 mL of methylene chloride and cooled in an ice bath. To this mixture was added 0.487 mg (0.003 mmoles) of 2,2,6, 6-tetramethyl-1-piperidinyloxy, free radical (TEMPO) and 0.014 mL (0.291 mmoles) of an aqueous KBr solution (5.95 g of KBr dissolved in 25 mL of water). The reaction mix was stirred vigorously while four 80 microliter portions of a 1M aqueous sodium hypochlorite (pH 9.5) were added at 15 minute intervals. After this time the reaction mixture was analyzed by TLC employing 90:10 chloroform:methanol to check for completeness of the reaction. If the reaction was not complete another portion of TEMPO and another regimen of the sodium hypochlorite solution should be added. This reaction required three additional regimens of TEMPO and sodium hypochlorite.

When the reaction was deemed complete by TLC, the layers were separated. The aqueous layer was extracted with methylene chloride (3×10 mL). The combined organic layer was washed with 10% HCl (1×10 mL), 30 mL of a 100 mL stock solution of 10% HCl containing 1.6 g of KI, 10% sodium thiosulfate (2×30 mL) and brine (1×30 mL). The organic layer was then dried over magnesium sulfate, filtered, and concentrated in vacuo. The crude material was triturated with petroleum ether to give an off-white solid which was recrystallized from ethyl acetate:hexane. There remained 0.048 g (48.5% yield) of a white solid with an Rf value of 0.43 in the solvent system detailed above.

TLC analysis of the product on silica gel gave an Rf value of 0.43 in the solvent system detailed above. HPLC analysis was performed on a Vydac C4 column (4.6×250 mm) at 60° C. using a gradient of 15–25% B/30 minutes (A=0.1% TFA in water, B=0.1% TFA in acetonitrile). The product had a retention time of 14.49 minutes and a purity of 97%.

Analyses of the final product provided the following results: Mass spectral analysis found (M+H)$^+$ at m/z 343. Elemental analysis for $C_{16}H_{30}N_4O_4$ found 55.80 C, 8.70 H and 15.97 N while calculated values were 56.12 C, 8.83 H and 16.36 N. For $^1$HNMR (600 MHz, d6-DMSO) analysis, the shifts observed were 8.65(t,1H), 8.10(d,1H), 6.07(d,1H), 4.85(m,1H), 4.20(m,1H), 3.12(m,2H), 2.77(s,6H), 1.77(m, 1H), 1.63(m,1H), 1.48(m,2H), 1.40(m,1H), 1.02(t,1H), 0.85(m,9H).

Example XIV—Boc-L-Leu-L-Abu-CONH-Et

Boc-L-Leu-L-Abu-CONH-Et was synthesized generally according to the procedure of Example XII with the exception of the synthesis of the reactant Boc-L-Leu-L-α-hydroxy-β-L-amino pentanoic acid ethyl amide.

Boc-Abu hydroxy ethyl amide (0.233 g, 894 mmoles) was dissolved in 5 mL of dioxane followed by the addition of 20 mL of 4N HCl/dioxane. The reaction mixture was allowed to react for two hours. After this time, the reaction mixture was concentrated in vacuo and used immediately in the next step. The α-hydroxy-β-L-amino pentanoic acid ethyl amide HCl salt prepared above, was dissolved in 25 mL of anhydrous DMF and cooled on an ice bath for ten minutes. To this solution was added 0.267 g (1.07 mmoles) of morpholinoleucine urea, 0.46 mL (2.68 mmoles) of diisopropylethylamine and 0.133 g (0.984 mmoles) of 1-hydroxybenzotriazole (HOBt) and allowed to equilibrate for thirty minutes. After this time 0.188 g (0.984 mmoles) of EDC suspended in 10 mL of anhydrous DMF was added and the reaction mixture was allowed to react overnight. The reaction mixture was concentrated in vacuo and the resulting residue redissolved in 100 mL of chloroform. The solution was washed twice with 50 mL of both saturated sodium bicarbonate and brine. The organic layer was dried over magnesium sulfate, filtered and concentrated in vacuo. The crude material was purified by silica gel column chromatography employing 90:10 chloroform:methanol as the eluent. There remained 0.1841 g (55.12% yield) of a white solid with and Rf value of 0.42 in the solvent system detailed above.

Boc-L-Leu-L-α-hydroxy-β-L-amino pentanoic acid ethyl amide (0.0823 g, 0.22 mmoles) was dissolved in 10 mL of methylene chloride and cooled in an ice bath. To this mixture was added 0.325 mg (0.002 mmoles) of 2,2,6,6-tetramethyl-1-piperidinyloxy, free radical (TEMPO) and 0.011 mL of an aqueous KBr solution (5.95 g of KBr dissolved in 25 mL of water). The reaction mix was stirred vigorously while four 60 microliter portions of an 1M aqueous sodium hypochlorite (pH 9.5) were added at 15 minute intervals. After this time the reaction mixture was analyzed by TLC employing 90:10 chloroform:methanol to check for completeness of the reaction. If the reaction was not complete another portion of TEMPO and another regimen of the sodium hypochlorite solution should be added. This reaction required one additional regiment of TEMPO and sodium hypochlorite.

When the reaction was deemed complete by TLC, the layers were separated. The aqueous layer was extracted with methylene chloride (3×10 mL). The combined organic layer was washed with 10% HCl (1×10 mL), 30 mL of a 100 mL stock solution of 10% HCl containing 1.6 g of KI, 10% sodium thiosulfate (2×30 mL) and brine (1×30 mL). The organic layer was then dried over magnesium sulfate, filtered and concentrated in vacuo. The crude material was triturated with petroleum ether to give an off-white solid which was recrystallized from ethyl acetate:hexane. There remained 0.067 g (82.3% yield) of a white solid with an Rf value of 0.52 in the solvent system detailed above.

TLC analysis of the product on silica gel gave an Rf value of 0.52 in the solvent system detailed above. HPLC analysis was performed on a Vydac C4 column (4.6×250 mm) at 60° C. using a gradient of 25–35% B/30 minutes (A=0.1% TFA in water, B=0.1% TFA in acetonitrile). The product had a retention time of 21.05 minutes and a purity of 99.14%.

Analyses of the final product provided the following results: Mass spectral analysis found $(M+H)^+$ at m/z 372. Elemental analysis for $C_{18}H_{33}N_3O_5$ found 57.84 C, 8.84 H and 11.05 N while calculated values were 58.20 C, 8.95 H and 11.05 N. For $^1$HNMR (600 MHz, d6-DMSO) analysis, the shifts observed were 8.66(t,1H), 8.06(d,1H), 6.85(d,1H), 4.88(m,1H), 3.99(m,1H), 3.12(m,2H), 1.77(m,1H), 1.77(m, 1H), 1.60(m,1H), 1.51(m,1H), 1.35(br s,11H), 1.02(t,3H), 0.86(m,9H).

Example
XV—Boc-D-Phe-L-Leu-L-Norvaline-CONH-Et

The α-hydroxy-β-L-hexanoic acid ethylamide hydrochloride salt was synthesized as described in Example I. The amide hydrochloride salt (4.75 mmol) was coupled to Boc-Leu-OH (5.22 mmol) by the following procedure. The Boc-Leu-OH was dissolved in 0.5M HOBt in DMF (10.4 mL, 5.2 mmol 1-hydroxybenzotriazole) and added to a flask containing EDC (1.0 g, 5.22 mmol) and the amine hydrochloride. To this mixture was added dimethylformamide (10 mL) and diisopropylethylamine (0.91 mL, 5.22 mmol) and the reaction was allowed to stir overnight at room temperature. The reaction solution was diluted into ethyl acetate (150 mL) and the resulting milky mixture was washed with 1N HCl (3×50 mL), saturated aqueous sodium bicarbonate (3×50 mL) and saturated aqueous chloride (1×50 mL). The organic phase was dried with anhydrous magnesium sulfate suction filtered and the filtrate was concentrated to a crystalline solid which was dried in vacuo (1.65 g, 4.26 mmol). Mass spectral analysis of this solid found $(M+H)^+ = 388$. Yield=89.6%.

The Boc protecting group was cleaved by dissolving the compound (4.26 mmol) in 4N HCl/dioxane (10 mL, 40 mmol HCl) and allowing the reaction to stir 30 min at room temperature. The reaction was concentrated to a white solid which was dried overnight in vacuo to provide the Leu-α-hydroxy-β-norvaline ethylamide hydrochloride salt in a quantitative yield. The Leu-α-hydroxy-β-norvaline ethylamide hydrochloride salt (0.93 mmol) was coupled to Boc-D-Phe (1.02 mmol) by the following procedure. In a 10 mL flask was placed the Boc-D-Phe, HOBt (156 mg, 1.02 mmol), EDC (195 mg, 1.02 mmol) and the amine hydrochloride. To this mixture was added dichloromethane (3 mL) and diisopropylethylamine (0.35 mL, 2 mmol) and the reaction was allowed to stir overnight at room temperature. The reaction solution was diluted into ethyl acetate (40 mL) and this was washed with 1N HCl (3×20 mL), saturated aqueous sodium bicarbonate (3×20 mL) and saturated aqueous sodium chloride (1×20 mL). The organic phase was dried with anhydrous magnesium sulfate, suction filtered and the filtrate was concentrated to a crystalline solid which was triturated with diethyl ether then isolated by suction filtration and dried overnight in vacuo to yield the product (320 mg, 0.6 mmol). Mass spectral analysis found $(M+H)^+$ =535. Elemental analysis found 62.51 C, 8.70 H and 10.34 N while calculated values were 62.90 C, 8.67 H and 10.48 N. $R_f$ (10% methanol/dichloromethane)=0.52. Yield=64%.

The Boc-D-Phe-L-Leu-β-amino-α-hydroxyethylamide was oxidized to the α-ketoamide by the following procedure. In a 25 mL round bottom flask was placed TEMPO (2 mg), potassium bromide (7 mg), water (30 uL) and methylene chloride (16 mL). As this mixture was stirred, the Boc-D-Phe-L-Leu-β-amino-α-hydroxyethylamide (305 mg, 0.57 mmol) was added and the reaction was stirred in an ice bath until the hydroxyamide was dissolved. To a 5.25% sodium hypochlorite solution (commercial bleach, 25 mL) was added sodium bicarbonate (300 mg) and this was stirred until the solid was dissolved. Over a period of approximately 5 minutes, 1.2 mL of the sodium hypochlorite solution was added with vigorous stirring to the above reaction mixture in an ice bath. The reaction mixture became a solid mass requiring the addition of 5 to 10 mL methylene chloride to obtain a slurry. After 20 min, another portion of TEMPO (2 mg) was added and more sodium hypochlorite solution was added as above. These additions were repeated two more times before the reaction was complete by TLC (no starting material remaining). The reaction was diluted into ethyl acetate (80 mL) and washed with 0.5N HCl (50 mL), potassium iodide (1.6 g) in 10% aqueous HCl (100 mL), 10% aqueous sodium thiosulfate (2×50 mL) and saturated sodium chloride (1×30 mL). The organic phase was dried with anhydrous magnesium sulfate, suction filtered and concentrated in vacuo to a white solid. This solid was vigorously stirred with ethyl ether (approx. 10 mL) and then isolated by suction filtration to obtain 222 mg (0.42 mmole). Mass spectral analysis found $(M+H)^+=533$. Elemental analysis found 62.74 C, 8.20 H and 10.34 N while calculated values were 63.10 C, 8.32 H and 10.52 N. $R_f$ (10% methanol/dichloromethane)=0.38. Yield=73%.

Example XVI—Boc-L-Phe-L-Leu-L-Norvaline-CONH-Et

The procedure described in Example XV was used to couple Boc-L-Phe to the amine to yield the Boc-L-Phe-L-Leu-β-amino-α-hydroxyamide (270 mg, 0.5 mmol). Mass spectral analysis found $(M+H)^+=535$. Elemental analysis found 62.75 C, 8.59 H and 10.41 N while calculated values were 62.90 C, 8.67 H and 10.48 N. $R_f$ (10% methanol/dichloromethane)=0.52 and 0.55 (2 diasteomers). Yield= 54%.

The Boc-L-Phe-L-Leu-β-amino-α-hydroxyethylamide (255 mg, 0.48 mmol) was oxidized to the α-ketoamide by the same procedure. Mass spectral analysis found $(M+H)^+=553$. Elemental analysis for $C_{23}H_{44}N_4O_6$ found 63.08 C, 8.10 H and 10.34 N while calculated values were 63.10 C, 8.32 H and 10.52 N. For $^1$HNMR (500 MHz, d6-DMSO) analysis, the shifts observed were: 0.77(d,3H); 0.81(d,4H); 0.84(t, 5H); 1.04(t,4H); 1.20(s,2H); 1.30(s,16H); 2.74(q, 1H); 2.86 (q,1H); 3.10(m,2H); 4.17(q,1H); 4.32(q,1H); 4.95(s,1H); 6.99(d,1H); 7.15(m,5H); 8.00(d,1H); 8.17(d, 1H). $R_f$ (5% methanol/dichloro-methane)=0.27. Yield=55%.

Example XVII—L-Phe-L-Leu-L-Norvaline-CONH-Et·HCl

The Boc protecting group was cleaved from the Boc-L-Phe-L-Leu-α-ketoamide (70 mg, 0.13 mmol) by dissolving in 4N HCl/dioxane (1 mL, 4mmol HCl) for 30 min at room temperature. The solvent was removed in vacuo and the resulting white solid was triturated with diethyl ether and dried in vacuo. Mass spectral analysis found $(M+H)^+=433$. Elemental analysis for $C_{23}H_{37}O_4N_4Cl$ found 63.08 C, 8.10 H and 10.34 N while calculated values were 63.10 C, 8.32 H and 10.52 N. For $^1$HNMR (500 MHz, d6-DMSO) analysis, the shifts observed were: 0.90(m,9H); 1.03(t,3H); 1.34(m,1H); 1.41–1.51(m,4H); 1.69(m,2H); 2.95(q,1H); 3.14(m,3H); 4.00(s,1H); 4.42(q,1H); 5.00(m,1H); 7.26(m, 5H); 8.20(s,3H); 8.45(d,1H); 8.70(m,2H). Yield=67%.

Example XVIII—D-Phe-L-Leu-L-Norvaline-CONH-Et·HCl

The Boc protecting group was cleaved from the Boc-D-Phe-L-Leu-α-ketoamide (100 mg, 0.19 mmol) by dissolving in 4NHCl/dioxane (1 mL, 4mmol HCl) for 30 min at room temperature. The solvent was removed in vacuo and the resulting white solid was triturated with diethyl ether and dried in vacuo. Mass spectral analysis found $(M+H)^+=433$. For $^1$HNMR (500 MHz, d6-DMSO) analysis, the shifts observed were: 0.73(d,3H); 0.78(d,3H); 0.87(t,3H); 1.03(t, 3H); 1.23(m,2H); 1.30(m,2H); 1.38(m,1H); 1.46–1.52 (m,1H); 1.67(m,1H); 3.01(q,2H); 3.11(m,2H); 4.10(s,1H); 4.30(m,1H); 4.92(m,1H); 7.27(m,5H); 8.33(s,3H); 8.45(d, 1H); 8.60(d,1H); 8.68(t,1H). Yield=60%.

MATERIALS AND INSTRUMENTATION

The Boc-amino acids and Cbz-amino acids were purchased from Bachem California. The TEMPO was purchased from Fluka. Silica gel for the ion exchange column was obtained from EM Science. All other reagents and solvents were purchased from Aldrich Chemical, Inc.

The ion exchange column was a Vydac C4 (250 mm×10 mm) column packed with silica gel, Dowex 50x8-100 (Aldrich Chemical, Inc.). The ion exchange column chromatography conditions were 60° C. with a flow rate of 3 ml/minute. Elution solvent A was composed of 0.1% TFA in water while solvent B was 0.1% TFA in $CH_3CN$. The elution was conducted as follows: 5 minutes with solvent A, 40 minutes with 75% solvent A and 25% solvent B, 1 minute with 65% solvent A and 35% solvent B, and then 5 minutes with solvent B.

The mass spectral analyses were performed by M-Scan, Inc. of West Chester, Pa. The $^1$H NMR analyses were performed by the National Center for NMR Application, Colorado State University.

CALPAIN ASSAY

Calpain activity was monitored using a continuous spectrofluorometric assay with succinyl-Leucyl-Tyrosyl-4-methylcoumaryl-γ-amide (SLY-MCA); Sasaki, T.; Kikuchi, T.; Yumotogo, N.; Yoshimura, N. and Murachi, T. J. Biol. Chem. 1984, 259. 12489–12494) at 25° C. using a Hitachi F4500 fluorescence spectrophotometer with a temperature controlled cuvette holder. The substrate solution was composed of SLY-MCA (2-0.2 mM) in 50 mM MOPS, pH 7.5, 5 mM $CaCl_2$, 5 mM β-mercaptoethanol and 1% DMSO. Solutions of the inhibitors (100–500 nM) were prepared in the same buffer mixture as substrate. Calpain I (porcine erythrocytes, Nacalai Tesque, Kyoto, Japan) was diluted to 180 ug/mL in 20 mM HEPES, pH 7.5, 2 mM EDTA, 2 mM EGTA and 5 mM DTT. The substrate solution (0.9 mL) was placed in a 1 cm cuvette and to this was added either the inhibitor solution (0.05 mL) or the buffer (0.05 mL) as a control. The reaction was initiated by addition of the calpain I solution (0.05 mL) and the increase in fluorescence (excitation at 380 nm; emission at 460 nm) was monitored for 3 to 10 min. The initial velocities were then used to obtain the values of Vmax, Km and Ki by an iterative least squares fit of the data to the following equation for competitive inhibition according to the method of W. W. Cleland, *Biochim. Biophys. Acta* 67: 173 (1963).

$$V=\{V_{max} \cdot [SLY-MCA]\}/\{(1+Inh]/KI) \cdot Km+[SLY-MCA]\}$$

The results of the Calpain I assays on the compounds synthesized in Examples I–XVIII are presented in Table I.

TABLE I

| Compound | Ki, pCal I(nM) |
|---|---|
| Cbz-L-Leu-L-Abu-CONH-Et | 77 ± 10 |
| Cbz-L-Leu-L-Norvaline-CONH-Et | 78 |
| Cbz-L-Leu-L-Phenylalanine-CONH-Et | 89 |
| Cbz-L-Leu-L-Phe-C(O)-Phe-OMe | 31 ± 12 |
| Cbz-L-Leu-L-Phe-C(O)-Tyr(O-t-butyl)-OMe | 273 ± 17 |

TABLE I-continued

| Compound | Ki, pCal I(nM) |
| --- | --- |
| Cbz-L-Leu-L-Phe-C(O)-L-α-Abu-OMe | 141 ± 22 |
| Cbz-L-Leu-L-Phe-C(O)-L-Norleucine-OMe | 76.6 ± 5.2 |
| Cbz-L-Leu-L-Phe-C(O)-L-Ala-OMe | 92 ± 6 |
| Cbz-L-Leu-L-Phe-C(O)-L-Ala-OH | 718 ± 84 |
| Cbz-L-Leu-L-Abu-C(O)-NH-(CH$_2$)$_2$-SO$_2$-ET | 129 ± 15 |
| Morpholinourea-L-Leu-L-Abu-CONH-Et | 199 ± 16 |
| Dimethylurea-L-Leu-L-Abu-CONH-Et | 332 ± 29 |
| Boc-L-Leu-L-Abu-CONH-Et | 170 ± 15 |
| Boc-D-Phe-L-Leu-L-Norvaline-CONH-Et | 93 ± 4 |
| Boc-L-Phe-L-Leu-L-Norvaline-CONH-Et | 61 ± 2 |
| L-Phe-L-Leu-L-Norvaline-CONH-Et.HCl | 116 ± 5 |
| D-Phe-L-Leu-L-Norvaline-CONH-Et.HCl | 244 ± 11 |

In addition, the IC$_{50}$ of Cbz-L-Leu-D-Phe-CONH-Et for porcine Calpain I was found to be greater than 1500 nM.

IN VIVO USE

Effective Calpain inhibitors can be used to treat human and mammalian neurodegenerative pathologies, such as stroke, head trauma, Alzheimer's and neural damage due to ischemia, while reducing the side-effects associated with the racemate.

For therapeutic use, the α-ketoamides may be administered orally, topically or parenterally. The term parenteral, as used herein, includes subcutaneous, intravenous, intramuscular, intrasternal injection or infusion techniques. The dosage depends primarily on the specific formulation and on the object of the therapy or prophylaxis.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Dosage levels of the order of 0.1 to 140 mg per kilogram of body weight per day are useful in the treatment of neurodegenerative pathologies. The amount of active ingredient that may be combined with carrier materials to produce a single dosage form will vary depending upon the host treated and the particular mode of administration.

For injection, the therapeutic amount of the α-ketoamides, or their pharmaceutically acceptable salts, will normally be in the dosage range from 0.1 to 140 mg per kilogram of body weight per day. Administration is made by intravenous, intramuscular or subcutaneous injection. In addition to the active ingredient, pharmaceutical compositions will usually contain a buffer to maintain the pH between about 3.5 to 7, and also sodium chloride, mannitol or sorbitol for adjusting isotonic pressure.

A composition for topical application can be formulated as an aqueous solution, lotion, jelly or an oily solution or suspension. A composition in the form of an aqueous solution is obtained by dissolving the α-ketoamide in aqueous buffer solution of pH 4 to 6.5, and if desired, adding a solubilizing agent. An oily formulation for topical application is obtained by suspending the compounds of this invention in an oil.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

We claim:
1. A compound represented by the formula:

$$M-AA^1_x-AA^2-AA^3-CO-NH-R^2-SO_2-R^3$$

and physiologically acceptable salts thereof, wherein

M is H, NH$_2$CO—, NH$_2$CS—, NH$_2$—SO$_2$—, R$^7$$_2$—NH—CO—, R$^7$$_2$N—CO—, R$^7$—NH—CS—, R$^7$$_2$N—CS—, R$^7$—NH—SO$_2$—, R$^7$$_2$N—SO$_2$—, R$^7$—CO—, R$^7$—CS—, R$^7$—SO$_2$—, C$_6$H$_5$CH$_2$—O—CO—, R$^7$—O—CO—, R$^7$—O—CS—, R$^8$N—CO—, R$^8$N—CS— or R$^8$N—SO$_2$—;

R$^7$ is a C$_{1-10}$ alkyl, C$_{1-10}$ fluoroalkyl, C$_{1-10}$ alkyl substituted with J, C$_{1-10}$ fluoroalkyl substituted with J, 1-adamantyl, 9-fluoroalkyl, phenyl substituted n times with K, naphthyl substituted n times with K, C$_{1-10}$ alkyl with an attached phenyl group substituted n times with K, C$_{1-10}$ alkyl with two attached phenyl groups substituted n times with K, C$_{1-10}$ alkyl with an attached phenoxy group, or C$_{1-10}$ alkyl with an attached phenoxy group substituted with K on the phenoxy group;

n is 0, 1, 2 or 3;

J is a halogen, hydroxyl, carboxy, cyano, amino, nitro, C$_{1-10}$ alkyloxy, C$_{1-10}$ alkylamino, C$_{2-12}$ dialkylamino, C$_{1-10}$ alkoxy-CO— group, C$_{1-10}$ alkoxy-NH— group, C$_{1-10}$ alkyl-S— group, or C$_{1-10}$ alkyl-SO$_2$— group;

K is a halogen, hydroxyl, carboxy, cyano, amino, nitro, C$_{1-10}$ alkyl, C$_{1-10}$ perfluoroalkyl, C$_{1-10}$ alkylamino, C$_{2-12}$ dialkylamino, C$_{1-10}$ alkoxy-CO— group, C$_{1-10}$ acyl, C$_{1-10}$ alkyloxy group, C$_{1-10}$ alkyl-S— group or C$_{1-10}$ alkyl-SO$_2$— group;

R$^8$N is a C$_{3-6}$ saturated or unsaturated heterocycle containing at least one nitrogen atom, said heterocycle can contain Q additional heteroatoms selected from the group consisting of nitrogen, oxygen, sulfur and combinations thereof, wherein said heterocycle can be substituted with one or more substituents selected from the group consisting of a hydroxyl, halogen, alkyl, cycloalkyl, aryl, alkoxy, alkoxycarbonyl, alkylthio and amino, Q is 0, 1 or 2;

AA$^1$ is an amino acid residue of a side chain blocked or unblocked amino acid, with the L configuration, D configuration or no chirality at the α-carbon, wherein said amino acid is selected from the group consisting of alanine, valine, leucine, isoleucine, proline, methionine, methionine sulfone, methionine sulfoxide, phenylalanine, tryptophan, glycine, serine, threonine, cysteine, tyrosine, asparagine, glutamine, aspartic acid, glutamic acid, lysine, arginine, histidine, phenylglycine, β-alanine, norleucine, norvaline, α-aminobutyric acid, ε-aminocaproic acid, citrulline, hydroxyproline, ornithine, homoarginine, sarcosine, indoline-2-carboxylic acid, 2-azetidine-carboxylic acid, pipecolinic acid, O-methylserine, O-ethylserine, S-methylcysteine, S-ethylcysteine, S-benzylcysteine, S-methylcysteine sulfone, S-ethylcysteine sulfone, S-benzylcysteine sulfone, cyclohexylalanine, homophenylalanine, p-chloro-phenylalanine, p-nitro-phenylalanine, p-amino-phenylalanine, 4-methoxy-phenylalanine, thienylalanine, pyridylalanine, NH$_2$—CH(CH$_2$CH(CH$_2$CH$_3$)$_2$)—COOH, α-aminoheptanoic acid, NH$_2$—CH(CH$_2$-1-naphthyl)—COOH, NH$_2$—CH(CH$_2$-2-naphthyl)—COOH, NH$_2$—CH(CH$_2$-cyclohexyl)—COOH, NH$_2$—CH(CH$_2$-cyclopentyl)—

COOH, NH$_2$—CH(CH$_2$-cyclobutyl)—COOH, NH$_2$—CH(CH$_2$-cyclopropyl-butyl)—COOH, trifluoroleucine or hexafluoroleucine;

x is 0, 1, 2 or 3;

AA$^2$ is an amino acid residue of a side chain blocked or unblocked amino acid, with the L and/or D configuration at the α-carbon, wherein said amino acid residue imparts calpain-specificity to calpain inhibitor molecules;

AA$^3$ is an amino acid residue of a side chain blocked or unblocked amino acid, with the L configuration at the α-carbon, wherein said amino acid is selected from the group consisting of alanine, α-aminobutyric acid, norvaline, valine, norleucine, leucine, phenylalanine, tyrosine, cyclohexylalanine, homophenylalanine, p-chloro-phenylalanine, p-nitro-phenylalanine, p-amino-phenylalanine, thienylalanine, lysine, ornithine, aspartic acid, glutamic acid, serine, threonine, pyridylalanine, 4-methoxy-phenylalanine or NHCH(R$^1$)CO;

R$^1$ is a branched or unbranched C$_{1-8}$ alkyl, cycloalkyl or fluoroalkyl;

R$^2$ is a branched or unbranched, saturated or unsaturated constituent selected from the group consisting of C$_{1-20}$ alkyl, C$_{1-20}$ cycloalkyl, C$_{1-20}$ alkyl with an attached phenyl group which is substituted n times with K, and C$_{1-20}$ cycloalkyl with an attached phenyl group which is substituted n times with K, and wherein said constituent can be substituted one or more times with Z;

Z is a hydroxyl, carboxy, alkoxy, alkoxymethoxy, alkanoate, alkyl, carbamyl, —O—CH$_2$—SO$_2$—CH$_3$ group, —OCH$_2$CH$_2$—O—CH$_2$CH$_2$—OH group, or —OCH$_2$CH$_2$—O—CH$_2$CH$_2$—OCH$_3$ group; and R$^3$ is R$^2$, —OH, —OR$^2$, —NH$_2$, —NHR$^2$ or —NR$^2$R$^2$.

2. A compound represented by the formula:

and physiologically acceptable salts thereof, wherein

M is H, NH$_2$—CO—, NH$_2$—CS—, NH$_2$—SO$_2$—, R$^7$—NH—CO—, R$^7_2$N—CO—, R$^7$—NH—CS—, R$^7_2$N—CS—, R$^7$—NH—SO$_2$—, R$^7_2$N—SO$_2$—, R$^7$—CO—, R$^7$—CS—, R$^7$—SO$_2$—, C$_6$H$_5$CH$_2$—O—CO—, R$^7$—O—CO—, R$^7$—O—CS—, R$^8$N—CO—, R$^8$N—CS— or R$^8$N—SO$_2$—;

R$^7$ is a C$_{1-10}$ alkyl, C$_{1-10}$ fluoroalkyl, C$_{1-10}$ alkyl substituted with J, C$_{1-10}$ fluoroalkyl substituted with J, 1-adamantyl, 9-fluoroalkyl, phenyl substituted n times with K, naphthyl substituted n times with K, C$_{1-10}$ alkyl with an attached phenyl group substituted n times with K, C$_{1-10}$ alkyl with two attached phenyl groups substituted n times with K, C$_{1-10}$ alkyl with an attached phenoxy group, or C$_{1-10}$ alkyl with an attached phenoxy group substituted with K on the phenoxy group;

n is 0, 1, 2 or 3;

J is a halogen, hydroxyl, carboxy, cyano, amino, nitro, C$_{1-10}$ alkyloxy, C$_{1-10}$ alkylamino, C$_{2-12}$ dialkylamino, C$_{1-10}$ alkoxy-CO— group, C$_{1-10}$ alkoxy-NH— group, C$_{1-10}$ alkyl-S— group, or C$_{1-10}$ alkyl-SO$_2$— group;

K is a halogen, hydroxyl, carboxy, cyano, amino, nitro, C$_{1-10}$ alkyl, C$_{1-10}$ perfluoroalkyl, C$_{1-10}$ alkylamino, C$_{2-12}$ dialkylamino, C$_{1-10}$ alkoxy-CO— group, C$_{1-10}$ acyl, C$_{1-10}$ alkyloxy group, C$_{1-10}$ alkyl-S— group or C$_{1-10}$ alkyl-SO$_2$— group;

R$^8$N is a C$_{3-6}$ saturated or unsaturated heterocycle containing at least one nitrogen atom. Said heterocycle can contain Q additional heteroatoms selected from the group consisting of nitrogen, oxygen, sulfur and combinations thereof, wherein said heterocycle can be substituted with one or more substituents selected from the group consisting of a hydroxyl, halogen, alkyl, cycloalkyl, aryl, alkoxy, alkoxycarbonyl, alkylthio and amino;

Q is 0, 1, or 2;

AA$^1$ is an amino acid residue of a side chain blocked or unblocked amino acid, with the L configuration, D configuration or no chirality at the α-carbon, wherein said amino acid is selected from the group consisting of alanine, valine, leucine, isoleucine, proline, methionine, methionine sulfone, methionine sulfoxide, phenylalanine, tryptophan, glycine, serine, threonine, cysteine, tyrosine, asparagine, glutamine, aspartic acid, glutamic acid, lysine, arginine, histidine, phenylglycine, β-alanine, norleucine, norvaline, α-aminobutyric acid, ε-aminocaproic acid, citrulline, hydroxyproline, ornithine, homoarginine, sarcosine, indoline-2-carboxylic acid, 2-azetidine-carboxylic acid, pipecolinic acid, O-methylserine, O-ethylserine, S-methylcysteine, S-ethylcysteine, S-benzylcysteine, S-methylcysteine sulfone, S-ethylcysteine sulfone, S-benzylcysteine sulfone, cyclohexylalanine, homophenylalanine, p-chloro-phenylalanine, p-nitro-phenylalanine, p-amino-phenylalanine, 4-methoxy-phenylalanine, thienylalanine, pyridylalanine, NH$_2$—CH(CH$_2$CH(CH$_2$CH$_3$)$_2$)—COOH, α-aminoheptanoic acid, NH$_2$—CH(CH$_2$-1-naphthyl)—COOH, NH$_2$—CH(CH$_2$-2 -naphthyl)—COOH, NH$_2$—CH(CH$_2$-cyclohexyl)—COOH, NH$_2$—CH(CH$_2$-cyclopentyl)—COOH, NH$_2$—CH(CH$_2$-cyclobutyl)—COOH, NH$_2$—CH(CH$_2$-cyclopropyl-butyl)—COOH, trifluoroleucine or hexafluoroleucine;

x is 0, 1, 2 or 3;

AA$^2$ is an amino acid residue of a side chain blocked or unblocked amino acid, with the L and/or D configuration at the α-carbon, wherein said amino acid residue imparts calpain-specificity to calpain inhibitor molecules;

AA$^3$ is an amino acid residue of a side chain blocked or unblocked amino acid, with the L configuration at the α-carbon, wherein said amino acid is selected from the group consisting of alanine, α-aminobutyric acid, norvaline, valine, norleucine, leucine, phenylalanine, tyrosine, cyclohexylalanine, homophenylalanine, p-chloro-phenylalanine, p-nitro-phenylalanine, p-amino-phenylalanine, thienylalanine, lysine, ornithine, aspartic acid, glutamic acid, serine, threonine, pyridylalanine, 4-methoxy-phenylalanine or NHCH(R$^1$)CO;

R$^1$ is a branched or unbranched C$_{1-8}$ alkyl, cycloalkyl or fluoroalkyl;

AA$^4$ is an amino acid residue of a side chain blocked or unblocked amino acid, with the L configuration, D configuration or no chirality at the α-carbon, wherein said amino acid is selected from the group consisting of glycine, β-alanine, alanine, α-aminobutyric acid, norvaline, valine, norleucine, leucine, phenylalanine, tyrosine, cyclohexylalanine, homophenylalanine, p-chloro-phenylalanine, p-nitro-phenylalanine, p-amino-phenylalanine, thienylalanine, lysine, ornithine, aspartic acid, glutamic acid, serine, threonine, pyridylalanine or 4-methoxy-phenylalanine; and $R^4$ is H, $C_{1-20}$ alkyl, aryl, $C_{1-20}$ alkyl with an attached phenyl group, or $C_{1-20}$ alkyl with an attached phenyl group substituted with K.

3. A method of forming an optically pure L-α-ketoamide from an L-β-amino-α-hydroxyamide comprising the steps of:
   a) mixing the L-β-amino-α-hydroxyamide in a solution containing a free radical catalyst; and
   b) mixing an oxidizing agent into said solution under conditions sufficient to form said optically pure L-α-ketoamide; and
   c) recovering said optically pure L-α-ketoamide from said solution.

4. The method of claim 3 wherein recovery of said optically pure L-α-ketoamide from said solution comprises the steps of:
   (i) separating said solution into an aqueous layer and an organic layer;
   (ii) extracting the aqueous layer with methylene chloride and combining the organic layers;
   (iii) washing the combined organic layer and drying said combined organic layer over anhydrous magnesium sulfate;
   (iv) filtering said combined organic layer and concentrating said combined organic layer in vacuo to a solid material;
   (v) mixing said solid material with ethyl ether and isolating said solid material by decanting the ethyl ether; and
   (vi) further purifying said solid material using reverse-phase HPLC.

5. A method of claim 3 further comprising the step of mixing the free radical catalyst, potassium bromide, water and methylene chloride to form said free radical catalyst solution.

6. A method of claim 3 wherein said free radical catalyst comprises 2,2,6,6-tetramethyl-1-piperidinyloxy.

7. A method of claim 3 wherein said oxidizing agent comprises a sodium hypochlorite solution.

8. A method of claim 7 wherein said sodium hypochlorite solution is buffered.

9. A method of claim 3 wherein said optically pure L-α-ketoamide is represented by the formula of claim 1.

10. A method of claim 3 wherein said optically pure L-α-ketoamide is represented by the formula of claim 2.

11. A method of claim 3 wherein said optically pure L α-ketoamide is represented by the formula:

M—AA$^1_x$—AA$^2$—AA$^3$—CO—NR$^5$R$^6$ and physiologically acceptable salts thereof, wherein M is H, $NH_2$—CO—, $NH_2$—CS—, $NH_2$—SO$_2$—, $R^7$—NH—CO—, $R^7{}_2$N—CO—, $R^7$—NH—CS—, $R^7{}_2$N—CS—, $R^7$—NH—SO$_2$, $R^7{}_2$N—SO$_2$—, $R^7$—CO—, $R^7$—CS—, $R^7$—SO$_2$—, $C_6H_5CH_2$—O—SO—, $R^7$—O—CO—, $R^7$—O—CS—, $R^8$N—CO—, $R^8$N—CS— or $R^8$N—SO$_2$—;

$R^7$ is a $C_{1-10}$ alkyl, $C_{1-10}$ fluoroalkyl, $C_{1-10}$ alkyl substituted with J, $C_{1-10}$ fluoroalkyl substituted with J, 1-adamantyl, 9-fluoroalkyl, phenyl substituted n times with K, naphthyl substituted n times with K, $C_{1-10}$ alkyl with an attached phenyl group substituted n times with K, $C_{1-0}$ alkyl with two attached phenyl groups substituted n times with K, $C_{1-10}$ alkyl with an attached phenoxy group, or $C_{1-10}$ alkyl with an attached phenoxy group substituted with K on the phenoxy group;

n is 0, 1, 2 or 3;

J is a halogen, hydroxyl, carboxy, cyano, amino, nitro, $C_{1-10}$ alkyloxy, $C_{1-10}$ alkylamino, $C_{2-12}$ dialkylamino, $C_{1-10}$ alkoxy-CO— group, $C_{1-10}$ alkoxy-NH— group, $C_{1-10}$ alkyl-S— group, or $C_{1-10}$ alkyl-SO$_2$— group;

K is a halogen, hydroxyl, carboxy, cyano, amino, nitro, $C_{1-10}$ alkyl, $C_{1-10}$ perfluoroalkyl, $C_{1-10}$ alkylamino, $C_{2-12}$ dialkylamino, $C_{1-10}$ alkoxy-CO— group, $C_{1-10}$ acyl, $C_{1-10}$ alkyloxy group, $C_{1-10}$ alkyl-S— group or $C_{1-10}$ alkyl-SO$_2$— group;

$R^8$N is a $C_{3-6}$ saturated or unsaturated heterocycle containing at least one nitrogen atom. Said heterocycle can contain Q additional heteroatoms selected from the group consisting of nitrogen, oxygen, sulfur and combinations thereof, wherein said heterocycle can be substituted with one or more substituents selected from the group consisting of a hydroxyl, halogen, alkyl, cycloalkyl, aryl, alkoxy, alkoxycarbonyl, alkylthio and amino;

Q is 0, 1, or 2;

AA$^1$ is an amino acid residue of a side chain blocked or unblocked amino acid, with the L configuration, D configuration or no chirality at the α-carbon, wherein said amino acid is selected from the group consisting of alanine, valine, leucine, isoleucine, proline, methionine, methionine sulfone, methionine sulfoxide, phenylalanine, tryptophan, glycine, serine, threonine, cysteine, tyrosine, asparagine, glutamine, aspartic acid, glutamic acid, lysine, arginine, histidine, phenylglycine, β-alanine, norleucine, norvaline, α-aminobutyric acid, ε-aminocaproic acid, citrulline, hydroxyproline, ornithine, homoarginine, sarcosine, indoline-2-carboxylic acid, 2-azetidine-carboxylic acid, pipecolinic acid, O-methylserine, O-ethylserine, S-methylcysteine, S-ethylcysteine, S-benzylcysteine, S-methylcysteine sulfone, S-ethylcysteine sulfone, S-benzylcysteine sulfone, cyclohexylalanine, homophenylalanine, p-chloro-pyridylalanine, p-nitro-phenylalanine, p-amino-phenylalanine, 4-methoxy-phenylalanine, thienylalanine, pyridylalanine, $NH_2$—CH(CH$_2$CH(CH$_2$CH$_3$)$_2$)—COOH—, α-aminoheptanoic acid, $NH_2$—CH(CH$_2$-1-naphthyl)—COOH, $NH_2$—CH(CH$_2$-2-naphthyl)—COOH, $NH_2$—CH(CH$_2$-cyclohexyl)—COOH, $NH_2$—CH(CH$_2$-cyclopentyl)—COOH, $NH_2$—CH(CH$_2$-cyclobutyl)—COOH, $NH_2$—CH(CH$_2$-cyclopropyl-butyl)—COOH, trifluoroleucine or hexafluoroleucine;

x is 0, 1, 2 or 3;

AA$^2$ is an amino acid residue of a side chain blocked or unblocked amino acid, with the L and/or D configuration at the α-carbon, wherein said amino acid residue imparts calpain-specificity to calpain inhibitor molecules;

AA$^3$ is an amino acid residue of a side chain blocked or unblocked amino acid, with the L configuration at the α-carbon, wherein said amino acid is selected from the group consisting of alanine, α-aminobutyric acid, norvaline, valine, norleucine, leucine, phenylalanine, tyrosine, cyclohexylalanine, homophenylalanine, p-chloro-phenylalanine, p-nitro-phenylalanine, p-amino-phenylalanine, thienylalanine, lysine, ornithine, aspartic acid, glutamic acid, serine, threonine, pyridylalanine, 4-methoxy-phenylalanine or NHCH(R$^1$)CO;

$R^1$ is a branched or unbranched $C_{1-8}$ alkyl, cycloalkyl or fluoroalkyl; and $R^5$ and $R^6$ are selected independently from the group consisting of H, $C_{1-20}$ alkyl, $C_{3-20}$ cycloalkyl, $C_{1-20}$ alkyl with an attached phenyl group which is substituted n times with K, and $C_{3-20}$ cycloalkyl with an attached phenyl group which is substituted n times with K, $C_{1-10}$ alkyl substituted with the nitrogen atom of a morpholine ring, $C_{1-10}$ alkyl substituted with the nitrogen atom of a piperidine ring, $C_{1-10}$ alkyl substituted with the nitrogen atom of a pyrrolidine ring, $C_{1-20}$-alkyl substituted with a hydroxyl group, $C_{1-10}$ alkyl substituted with a 2-pyridyl group, $C_{1-10}$ alkyl substituted with a 3-pyridyl group, $C_{1-10}$ alkyl substituted with a 4-pyridyl group, $C_{1-10}$ alkyl substituted with a cyclohexyl group, —NH—$CH_2CH_2$—(4-hydroxyphenyl) and —NH—$CH_2CH_2$—(3-indolyl).

12. A compound represented by the formula:

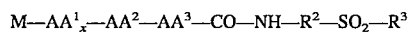

$$M-AA^1_x-AA^2-AA^3-CO-NH-R^2-SO_2-R^3$$

and physiologically acceptable salts thereof, wherein

M is H or an amine protecting group;

$AA^1$ is an amino acid residue of a side chain blocked or unblocked amino acid, with the L configuration, D configuration or no chirality at the α-carbon, wherein said amino acid is selected from the group consisting of alanine, valine, leucine, isoleucine, proline, methionine, methionine sulfone, methionine sulfoxide, phenylalanine, tryptophan, glycine, serine, threonine, cysteine, tyrosine, asparagine, glutamine, aspartic acid, glutamic acid, lysine, arginine, histidine, phenylglycine, β-alanine, norleucine, norvaline, α-aminobutyric acid, ε-aminocaproic acid, citrulline, hydroxyproline, ornithine, homoarginine, sarcosine, indoline-2-carboxylic acid, 2-azetidine-carboxylic acid, pipecolinic acid, O-methylserine, O-ethylserine, S-methylcysteine, S-ethylcysteine, S-benzylcysteine, S-methylcysteine sulfone, S-ethylcysteine sulfone, S-benzylcysteine sulfone, cyclohexylalanine, homophenylalanine, p-chloro-phenylalanine, p-nitro-phenylalanine, p-amino-phenylalanine, 4-methoxy-phenylalanine, thienylalanine, pyridylalanine, $NH_2CH(CH_2CH(CH_2CH_3)_2)$—COOH, α-aminoheptanoic acid, $NH_2$—$CH(CH_2$-1-naphthyl)—COOH, $NH_2$—$CH(CH_2$-2-naphthyl)—COOH, $NH_2$—$CH(CH_2$-cyclohexyl)—COOH, $NH_2$—$CH(CH_2$-cyclopentyl)—COOH, $NH_2$—$CH(CH_2$-cyclobutyl)—COOH, $NH_2$—$CH(CH_2$-cyclopropyl-butyl)—COOH, trifluoroleucine or hexafluoroleucine;

x is 0, 1, 2 or 3;

$AA^2$ is a (D)-amino acid, an (L)-amino acid or a (D,L)-amino acid which imparts calpain-specificity to calpain inhibitor molecules;

$AA^3$ is an (L)-amino acid selected from the group consisting of alanine, α-aminobutyric acid, norvaline, valine, norleucine, leucine, phenylalanine, tyrosine, cyclohexylalanine, homophenylalanine, p-chloro-phenylalanine, p-nitro-phenylalanine, p-amino-phenylalanine, thienylalanine, lysine, ornithine, aspartic acid, glutamic acid, serine, threonine, pyridylalanine, 4-methoxy-phenylalanine and $NHCH(R^1)CO$;

$R^1$ is a branched or unbranched $C_{1-8}$ alkyl, cycloalkyl or fluoroalkyl;

$R^2$ is a branched or unbranched, saturated or unsaturated constituent selected from the group consisting of $C_{1-20}$ alkyl, $C_{3-20}$ cycloalkyl, $C_{1-20}$ alkyl with an attached phenyl group which is substituted n times with K, and $C_{3-20}$ cycloalkyl with an attached phenyl group which is substituted n times with K, and wherein said constituent can be substituted one or more times with Z;

Z is a hydroxyl, carboxy, alkoxy, alkoxymethoxy, alkanoate, alkyl, carbamyl, —O—$CH_2$—$SO_2$—$CH_3$ group, —$OCH_2CH_2$—O—$CH_2CH_2$—OH group, or —$OCH_2CH_2$—O—$CH_2CH_2$—$OCH_3$ group;

$R^3$ is $R^2$, —OH, —$OR^2$, —$NH_2$, —$NHR^2$ or —$NR^2R^2$;

n is 0, 1, 2, or 3; and

K is halogen, hydroxyl, carboxy, cyano, amino, nitro, $C_{1-10}$ alkyl, $C_{1-10}$ perfluoroalkyl, $C_{1-10}$ alkylamino, $C_{2-12}$ dialkylamino, $C_{1-10}$ alkoxy-CO—, $C_{1-10}$ acyl, $C_{1-10}$ alkyloxy, $C_{1-10}$ alkyl-S— or $C_{1-10}$ alkyl-$SO_2$—.

13. A compound represented by the formula:

$$M-AA^1_x-AA^2-AA^3-CO-AA^4-OR^4$$

and physiologically acceptable salts thereof, wherein

M is H or an amine protecting group;

$AA^1$ is an amino acid residue of a side chain blocked or unblocked amino acid, with the L configuration, D configuration or no chirality at the α-carbon, wherein said amino acid is selected from the group consisting of alanine, valine, leucine, isoleucine, proline, methionine, methionine sulfone, methionine sulfoxide, phenylalanine, tryptophan, glycine, serine, threonine, cysteine, tyrosine, asparagine, glutamine, aspartic acid, glutamic acid, lysine, arginine, histidine, phenylglycine, β-alanine, norleucine, norvaline, α-aminobutyric acid, ε-aminocaproic acid, citrulline, hydroxyproline, ornithine, homoarginine, sarcosine, indoline-2-carboxylic acid, 2-azetidine-carboxylic acid, pipecolinic acid, O-methylserine, O-ethylserine, S-methylcysteine, S-ethylcysteine, S-benzylcysteine, S-methylcysteine sulfone, S-ethylcysteine sulfone, S-benzylcysteine sulfone, cyclohexylalanine, homophenylalanine, p-chloro-phenylalanine, p-nitro-phenylalanine, p-amino-phenylalanine, 4-methoxy-phenylalanine, thienylalanine, pyridylalanine, $NH_2$—$CH(CH_2CH(CH_2CH_3)_2)$—COOH, α-aminoheptanoic acid, $NH_2$—$CH(CH_2$-1-naphthyl)—COOH, $NH_2$—$CH(CH_2$-2-naphthyl)—COOH, $NH_2$—$CH(CH_2$-cyclohexyl)—COOH, $NH_2$—$CH(CH_2$-cyclopentyl)—COOH, $NH_2$—$CH(CH_2$-cyclobutyl)—COOH, $NH_2$—$CH(CH_2$-cyclopropyl-butyl)—COOH, trifluoroleucine or hexafluoroleucine;

x is 0, 1, 2 or 3;

$AA^2$ is (D)-amino acid, an (L)-amino acid, or a (D,L)-amino acid which imparts calpain-specificity to calpain inhibitor molecules;

$AA^3$ is an (L)-amino acid selected from the group consisting of alanine, α-aminobutyric acid, norvaline, valine, norleucine, leucine, phenylalanine, tyrosine, cyclohexylalanine, homophenylalanine, p-chloro-phenylalanine, p-nitro-phenylalanine, p-amino-phenylalanine, thienylalanine, lysine, ornithine, aspartic acid, glutamic acid, serine, threonine, pyridylalanine, 4-methoxy-phenylalanine or $NHCH(R^1)CO$;

$R^1$ is a branched or unbranched $C_{1-8}$ alkyl, cycloalkyl or fluoroalkyl;

$AA^4$ is a (D)-amino acid, an (L)-amino acid or a (D,L)-amino acid selected from the group consisting of glycine, alanine, alanine, α-aminobutyric acid, norvaline, valine, norleucine, leucine, phenylalanine, tyrosine, cyclohexylalanine, homophenylalanine, p-chloro-phenylalanine, p-nitro-phenylalanine, p-amino-phenylalanine, thienylalanine, lysine, ornithine, aspartic acid, glutamic acid, serine, threonine, pyridylalanine or 4-methoxy-phenylalanine; and $R^4$ is H, $C_{1-20}$ alkyl, aryl, $C_{-20}$ alkyl with an attached phenyl group, or $C_{1-20}$ alkyl with an attached phenyl group substituted with K; and n is 0, 1, 2 or 3; and K is halogen, hydroxyl, carboxy, cyano, amino, nitro, $C_{1-10}$ alkyl, $C_{1-10}$ perfluoroalkyl, $C_{1-10}$ alkylamino, $C_{2-12}$ dialkylamino, $C_{1-10}$ alkoxy-CO—, $C_{1-10}$ acyl, $C_{1-10}$ alkyloxy, $C_{1-10}$ alkyl-S— or $C_{1-10}$ alkyl-SO$_2$—.

* * * * *